(12) United States Patent
Jansen et al.

(10) Patent No.: US 10,532,990 B2
(45) Date of Patent: Jan. 14, 2020

(54) METHODS FOR CONVERTING CELLULOSE TO FURANIC PRODUCTS

(71) Applicant: VIRDIA, INC., Raceland, LA (US)

(72) Inventors: Robert Jansen, Collinsville, IL (US); James Alan Lawson, Ellsworth, ME (US); Philip Travisano, Danville, VA (US); Brendon Christopher Stout, Burlington, NC (US); Allison Jean Hulchanski, Chapel Hill, NC (US); Neta Matis, Danville, VA (US); Noa Lapidot, Mevaserat Zion (IL); Michael Zviely, Haifa (IL); Adam Tyler Carden, Henderson, NC (US); Michael Andrew Faison, Danville, VA (US); Bassem Hallac, Jersualem (IL); Sterling Alexander White, Rocky Mount, VA (US)

(73) Assignee: VIRDIA, INC., Raceland, LA (US)

( * ) Notice: Subject to any disclaimer, the term of this patent is extended or adjusted under 35 U.S.C. 154(b) by 0 days.

(21) Appl. No.: 15/527,597

(22) PCT Filed: Dec. 11, 2015

(86) PCT No.: PCT/US2015/065403
§ 371 (c)(1),
(2) Date: May 17, 2017

(87) PCT Pub. No.: WO2016/094878
PCT Pub. Date: Jun. 16, 2016

(65) Prior Publication Data
US 2017/0362194 A1    Dec. 21, 2017

Related U.S. Application Data

(60) Provisional application No. 62/091,319, filed on Dec. 12, 2014, provisional application No. 62/095,673, filed on Dec. 22, 2014.

(51) Int. Cl.
| | | |
|---|---|---|
| C07D 307/50 | (2006.01) | |
| C13K 1/04 | (2006.01) | |
| C13K 11/00 | (2006.01) | |
| C07D 233/58 | (2006.01) | |

(52) U.S. Cl.
CPC ......... *C07D 307/50* (2013.01); *C07D 233/58* (2013.01); *C13K 1/04* (2013.01); *C13K 11/00* (2013.01)

(58) Field of Classification Search
CPC .................................................. C07D 307/50
See application file for complete search history.

(56) References Cited

U.S. PATENT DOCUMENTS

| | | | |
|---|---|---|---|
| 3,684,574 A | 8/1972 | Edward et al. | |
| 4,618,579 A | 10/1986 | Dwiggins et al. | |
| 4,764,596 A | 8/1988 | Lora et al. | |
| 6,177,575 B1 | 1/2001 | Arduengo, III et al. | |
| 6,518,440 B2 | 2/2003 | Lightner | |
| 7,897,794 B2* | 3/2011 | Geier ................... | C07D 307/46 549/488 |
| 8,722,878 B2 | 5/2014 | Raines et al. | |
| 8,790,542 B2 | 7/2014 | Dibble et al. | |
| 8,816,131 B2 | 8/2014 | Chen et al. | |
| 9,157,130 B2 | 10/2015 | Brennan et al. | |
| 2002/0123636 A1 | 9/2002 | Lightner | |
| 2009/0270608 A1 | 10/2009 | Zhang et al. | |
| 2009/0277841 A1 | 11/2009 | Johnson et al. | |
| 2010/0196967 A1 | 8/2010 | Edye et al. | |
| 2011/0065159 A1* | 3/2011 | Raines .................... | C08B 1/003 435/163 |
| 2013/0204039 A1* | 8/2013 | Runge .................... | C07C 51/00 562/515 |
| 2013/0274456 A1 | 10/2013 | Parekh et al. | |
| 2014/0190471 A1 | 7/2014 | Zhang et al. | |
| 2014/0235851 A1 | 8/2014 | Binder et al. | |
| 2014/0371473 A1 | 12/2014 | Blank et al. | |

FOREIGN PATENT DOCUMENTS

| | | |
|---|---|---|
| CN | 101720320 A | 6/2010 |
| CN | 102066304 A | 5/2011 |
| EP | 2813494 A1 | 12/2014 |
| JP | 07165781 A  * | 6/1995 |
| JP | 2010516750 A | 5/2010 |
| WO | WO-2008157617 A1 | 12/2008 |
| WO | WO-2013166237 A1 | 11/2013 |
| WO | WO-2013166469 A2 | 11/2013 |
| WO | WO-2014138600 A1 | 9/2014 |
| WO | WO-2014178911 A1 | 11/2014 |
| WO | WO-2016094878 A1 | 6/2016 |

OTHER PUBLICATIONS

Su et al. Applied Catalysis A: General 2009, 361, 117-122 (Year: 2009).*
Binder et al. J. Am. Chem. Soc. 2009, 131, 1979-1985 (Year: 2009).*
Caes, Benjamin Richard. Catalytic systems for carbohydrate conversions. Ph.D. Thesis, 2012, University of Wisconsin-Madison, 196 pages (Year: 2012).*
Mosier et al. Bioresource Technology 2005, 96, 673-686 (Year: 2005).*
MacDonald et al. Biotechnology and Bioengineering 1983, 25, 2067-2076 (Year: 1983).*
Qu et al. Ind. Eng. Chem. Res. 2012, 51, 13008-13013 (Year: 2012).*

(Continued)

*Primary Examiner* — Matthew P Coughlin
(74) *Attorney, Agent, or Firm* — Wilson Sonsini Goodrich & Rosati

(57) ABSTRACT

The present invention relates to systems, methods, and processes for the production of conversion products such as furanic products from biomass such as lignocellulosic materials.

24 Claims, 12 Drawing Sheets

(56) References Cited

OTHER PUBLICATIONS

Mercadier et al. J. Chem. Tech. Biotechnol. 1981, 31, 489-496 (Year: 1981).*
Takagaki et al. Chem. Commun. 2009, 6276-6278 (Year: 2009).*
Saari et al. Chem. Eng. Technol. 2011, 34, 282-288 (Year: 2011).*
EP15867656.9 Extended European Search Report dated Jun. 6, 2018.
Li et al. The dehydration of fructose to 5-hydroxymethylfurfural efficiently catalyzed by acidic ion-exchange resin in ionic liquid. Bioresource Technology vol. 133 (Jan. 22, 2013). DOI: 10.1016/j.biortech.2013.01.038.
Qi et al. Catalytic conversion of cellulose into 5-hydroxymethylfurfural in high yields via a two-step process. Cellulose 18(5):1327-1333 (Jun. 19, 2011). DOI: 10.1007/S10570-011-9568-1.
Qi et al. Efficient process for conversion of fructose to 5-hydroxymethylfurfural with ionic liquids. Green Chemistry 11:1327-1331 (Jun. 30, 2009).
Qi et al. Fast Transformation of Glucose and Di-/Polysaccharides into 5-Hydroxymethylfurfural by Microwave Heating in an Ionic Liquid/Catalyst System. ChemSusChem 3(9):1071-1077 (Sep. 24, 2010). DOI: 10.1002/cssc.201000124.
Qu et al. Alkaline Ionic Liquids as Catalysts: A Novel and Green Process for the Dehydration of Carbohydrates to Give 5-Hydroxymethylfurfural. Industrial & Engineering Chemistry Research 51(40):13008-13013 (Oct. 10, 2012). DOI: 10.1021/ie300140g.
Takagaki et al. A one-pot reaction for biorefinery: combination of solid acid and base catalysts for direct production of 5-hydroxymethylfurfural from saccharides. Chemical Communications 41(1):6276 (Jan. 1, 2009). DOI: 10.1039/B914087e.
Wang et al. Catalytic hydrolysis of lignocellulosic biomass into 5-hydroxymethylfurfural in ionic liquid. Bioresource Technology 102(5):4179-4183 (Dec. 17, 2010). DOI: 10.1016/J.BIORTECH.2010.12.073.
Caes, Benjamin Richard. Catalytic systems for carbohydrate conversions. Ph.D. Thesis, 2012. University of Wisconsin-Madison. 196 pages.
Mai et al. Recovery of ionic liquid and sugars from hydrolyzed biomass using ion exclusion simulated moving bed chromatography. Journal of Chromatography A. vol. 1227, Mar. 2, 2012, pp. 67-72.
Román-Leshkov et al. Solvent Effects on Fructose Dehydration to 5-Hydroxymethylfurfural in Biphasic Systems Saturated with Inorganic Salts. Topics in Catalysis. Apr. 2009, vol. 52, Issue 3, pp. 297-303.
Su et al. Single-step conversion of cellulose to 5-hydroxymethylfurfural (HMF), a versatile platform chemical. Applied Catalysis A: General. vol. 361, Issues 1-2, Jun. 20, 2009, pp. 117-122.
Upare, et al. An integrated process for the production of 2,5-dimethylfuran from fructose. Green Chem. 2015; 17:3310-3313.
Zhang et al. Preparation of Lignin. Cellulose Biomass Hydrolysis and Application Thereof, pp. 224-229. Dec. 31, 2012.
Zhao. Production of fructose syrup. Cereal and Oil Technology, pp. 154-158. Nov. 30, 2004.

* cited by examiner

METHODS FOR CONVERTING CELLULOSE TO FURANIC PRODUCTS

CROSS REFERENCE TO RELATED APPLICATIONS

This application is a National Stage Entry of PCT/US2015/065403, filed Dec. 11, 2015, which claims the benefit of U.S. Provisional Application No. 62/091,319, filed Dec. 12, 2014, and U.S. Provisional Application No. 62/095,673 filed Dec. 22, 2014, each of which is incorporated herein by reference in its entirety for all purposes.

BACKGROUND OF THE INVENTION

Hydroxymethyl furfural (HMF) and di-substituted furanic derivatives are key intermediate chemicals in a production chain based on renewable carbon sources, e.g., lignocellulosic biomass. Efficient, scalable processes and methods that utilize lignocellulosic biomass at high yields in order to produce hydroxymethyl furfural and di-substituted furanic derivatives are desirable.

SUMMARY OF THE INVENTION

The present disclosure provides for processes, methods, systems, and compositions for efficiently utilizing biomass for the production of hydroxymethyl furfural, di-substituted furanic derivatives, and saccharides.

Provided herein are processes for conversion of cellulose pulp to hydroxymethyl furfural. The processes can comprise: separating a lignin-depleted hydrolysate stream comprising sodium ions in an amount not greater than 5% to thereby produce a first stream comprising water and hydroxymethyl furfural; a second stream comprising water and glucose; and a third stream comprising water and cellobiose; isomerizing the glucose in the second stream to thereby produce fructose; and dehydrating the fructose to thereby produce a reaction product comprising the hydroxymethyl furfural.

In the processes disclosed herein, the processes can further comprise: conditioning the cellulose pulp in a solvent to thereby form a conditioned pulp; hydrolyzing the conditioned pulp in an aqueous solution comprising an acid catalyst to thereby produce a hydrolysate stream; and removing at least some lignin from the hydrolysate stream to thereby produce the lignin-depleted hydrolysate stream and a lignin-enriched composition, the removing comprising controlling a pH of the aqueous solution and diluting the aqueous solution with water; wherein the conditioning, the hydrolyzing, and the removing occurs prior to the separating, the isomerizing, and the dehydrating.

In the processes disclosed herein, the solvent can comprise ionic liquid. In the processes disclosed herein, the second stream comprises ionic liquid and the third stream comprises ionic liquid. In the processes disclosed herein, the process can further comprise diverting the lignin-depleted hydrolysate stream from a first vessel to a second vessel prior to the separating, the isomerizing, and the dehydrating. In the processes disclosed herein, the processes can further comprise recycling the reaction product, the recycling comprising introducing the reaction product from the dehydrating to the separating. In the processes disclosed herein, the processes can further comprise capturing the hydroxymethyl furfural from the reaction product, the capturing comprising adsorbing on a non-functional polymer the hydroxymethyl furfural from the reaction product; and recovering the hydroxymethyl furfural, the recovering comprising solvent desorption. In the processes disclosed herein, the reaction product can comprise an organic acid.

In the processes disclosed herein, the capturing can further comprise controlling a pH of the reaction product to be above the pKa of the organic acid such that water and organic anions are not adsorbed on the non-functional polymer. In the processes disclosed herein, the pH of the reaction product can be controlled to be above 5.8. In the processes disclosed herein, the ionic liquid can be selected from 1-ethyl-3-methylimidazolium chloride or 1-butyl-3-methylimidazolium chloride. In the processes disclosed herein, the processes can further comprise converting the ionic liquid to an ionic liquid in hydroxide form, the converting comprising contacting an aqueous ionic liquid solution comprising the ionic liquid with a strong base anion exchange resin in hydroxide form. In the processes disclosed herein, the isomerizing can comprise controlling pH, the controlling comprising using the ionic liquid in hydroxide form as a base. In the processes disclosed herein, the isomerizing can be catalyzed by the ionic liquid in hydroxide form. In the processes disclosed herein, the ionic liquid in hydroxide form can form an ionic liquid in chloride form that is used for the dehydrating.

Provided herein are methods to recycle ionic liquid in a closed process loop. The methods can comprise: contacting a dilute aqueous stream comprising imidazolium cation with a resin, the contacting comprising adsorbing the imidazolium cation on the resin, wherein the resin is a weak acid cation exchange resin in the deprotonated form; desorbing the imidazolium cation, the desorbing comprising contacting the resin with a solution comprising hydrochloric acid; and reintroducing the solution and imidazolium cation to the closed process loop for further use.

In the methods disclosed herein, the closed process loop can be used to couple an isomerization reaction to a dehydration reaction. In the methods disclosed herein, the isomerization reaction can comprise isomerizing glucose to form fructose, and wherein the dehydration reaction comprises dehydrating fructose to form hydroxymethyl furfural.

Provided herein are systems for converting glucose to hydroxymethyl furfural. The systems can comprise: a chromatography separation unit configured to separate a stream comprising sodium ions in an amount not greater than 5% into a first stream, a second stream, and a third stream; the first stream comprising water and hydroxymethyl furfural; the second stream comprising water and glucose; and the third stream comprising water and cellobiose; an isomerization unit configured to perform the isomerization of glucose to fructose, the isomerization comprising treating the second stream with a base to thereby produce a base-treated second stream; and a dehydration unit configured to dehydrate the fructose to hydroxymethyl furfural.

In the systems disclosed herein, the second stream can comprise ionic liquid and the third stream comprises ionic liquid. In the systems disclosed herein, the systems can further comprise a second chromatography separation unit configured to perform a separation of the second stream to thereby produce a product stream comprising glucose. In the systems disclosed herein, the systems can further comprise a glucose refining unit configured to refine the product stream comprising glucose to a glucose product, the glucose refining unit comprising at least one unit selected from a strong acid cation resin, an anion exchanger, an activated carbon resin, or an evaporation unit. In the systems disclosed herein, the product stream can comprise glucose comprises at least 60% glucose (weight/weight).

Disclosed herein are processes to convert cellulose to hydroxymethyl furfural. The processes can comprises producing at least 60 g of hydroxymethyl furfural as an output for each 100 g of cellulose provided as an input.

In the processes disclosed herein, at least 63 g of hydroxymethyl furfural can produced as an output for each 100 g of cellulose provided as an input. In the processes disclosed herein, at least 65 g of hydroxymethyl furfural can be produced as an output for each 100 g of cellulose provided as an input. In the processes disclosed herein, at least 67 g of hydroxymethyl furfural can be produced as an output for each 100 g of cellulose provided as an input. In the processes disclosed herein, the processes can comprise hydrolyzing the cellulose to a first sugar stream comprising at least 80% glucose (weight/dry solids). In the processes disclosed herein, the hydrolyzing can occur in an ionic liquid. In the processes disclosed herein, the ionic liquid can be selected from 1-butyl-3-methylimidazolium chloride or 1-ethyl-3-methylimidazolium chloride. In the processes disclosed herein, the first sugar stream can comprise cellobiose, hydroxymethyl furfural, and organic acids.

In the processes disclosed herein, the processes can further comprise chromatographically separating a second sugar stream comprising hydroxymethyl furfural, cellobiose, ionic liquid, glucose, and fructose; the chromatographically separating comprising using sequential simulated moving bed chromatography. In the processes disclosed herein, the chromatographically separating can produce a first output stream, a second output stream, and a third output stream; the first output stream comprising hydroxymethyl furfural; the second output stream comprising ionic liquid and glucose; and the third output stream comprising ionic liquid and cellobiose. In the processes disclosed herein, the sequential simulated moving bed chromatography can use an industrial grade resin comprising bead sizes of at least 300 micron. In the processes disclosed herein, the processes can comprise treating the second output stream with base, the treating comprising isomerizing at least a portion of the glucose to fructose to thereby produce a base-treated second stream. In the processes disclosed herein, the base can comprise the ionic liquid, wherein the ionic liquid is in hydroxide form.

In the processes disclosed herein, the processes can further comprise treating the base-treated second stream, the treating comprising dehydrating the fructose to hydroxymethyl furfural to thereby produce a dehydrated second stream, the dehydrating comprising using a dehydrating agent. In the processes disclosed herein, not greater than 10% of the glucose present in the base-treated second stream can be reacted with the dehydrating agent.

In the processes disclosed herein, the processes can further comprise isolating hydroxymethyl furfural, the isolating comprising at least one of: treating the dehydrated second stream, the treating comprising using a hydrophobic resin to thereby capture hydroxymethyl furfural; desorbing the captured hydroxymethyl furfural from the hydrophobic resin, the desorbing comprising contacting the loaded resin with solvent S2; adding an organic solvent; and distilling the solvent S2 using azeotropic distillation. In the processes disclosed herein, solvent S2 can be ethyl acetate.

In the processes disclosed herein, the processes can further comprise recycling the ionic liquid, the recycling comprising: treating a first portion of an ionic liquid stream with a weak acid cation exchange resin to thereby form a weak acid cation exchange resin treated stream; adding solvent to the weak acid cation exchange resin treated stream; distilling the solvent and water to thereby form a dehydrated ionic liquid stream; and introducing the ionic liquid from the dehydrated ionic liquid stream into the process. In the processes disclosed herein, the ionic liquid from the dehydrated ionic liquid stream can be introduced into a reactor comprising cellulose, and wherein the cellulose is hydrolyzed to glucose in the reactor. In the processes disclosed herein, the processes can further comprise recycling the ionic liquid, the recycling comprising treating a stream comprising ionic liquid with a weak acid cation exchange resin to thereby produce a resin treated stream comprising ionic liquid; and reintroducing the ionic liquid from the resin treated stream into the process. In the processes disclosed herein, the ionic liquid from the resin treated stream can be reintroduced to a composition comprising at least 70% glucan (weight/dry solids). In the processes disclosed herein, at least 99% of the ionic liquid can be recycled to thereby produce recycled ionic liquid. In the processes disclosed herein, the recycled ionic liquid can comprise glucose or cellobiose.

Provided herein are furfural product compositions. The furfural product compositions can comprise at least 5% hydroxymethyl furfural (weight/weight) and an amount not greater than 95% of a solvent (weight/weight), wherein the solvent is selected from 2-butanol, 2-propanol, tetralin, or water, or a combination thereof. In the furfural product compositions disclosed herein, the furfural product compositions can further comprise at least 50 ppb of a marker molecule, wherein the marker molecule is selected from ethyl acetate, ionic liquid cation, furfural, levulinate anion, formate anion, levulinic acid, formic acid, glucose, fructose, or mannose.

Provided herein are ionic liquid stream compositions. The ionic liquid stream compositions can comprise i) at least 95% ionic liquid (weight/weight); ii) from 0.1 to 2% cellobiose (weight/weight); iii) an amount not greater than 0.1% fructose (weight/weight); iv) an amount not greater than 0.1% hydroxymethyl furfural (weight/weight); v) an amount not greater than 4% water (weight/weight); and vi) an amount not greater than 2% solvent S3 (weight/weight).

In the ionic liquid stream compositions disclosed herein, the ionic liquid stream compositions can further comprise at least one of the following characteristics: i) from 0.1 to 3% glucose (weight/weight); ii) an amount not greater than 0.1% mannose (weight/weight); iii) an amount not greater than 0.1% levulinic acid (weight/weight); and iv) an amount not greater than 0.1% formic acid (weight/weight). In the ionic liquid stream compositions disclosed herein, the ionic liquid stream compositions can further comprise at least two of the following characteristics: i) from 0.1 to 3% glucose (weight/weight); ii) an amount not greater than 0.1% mannose (weight/weight); iii) an amount not greater than 0.1% levulinic acid (weight/weight); and iv) an amount not greater than 0.1% formic acid (weight/weight). In the ionic liquid stream compositions disclosed herein, the ionic liquid stream compositions can further comprise at least three of the following characteristics: i) from 0.1 to 3% glucose (weight/weight); ii) an amount not greater than 0.1% mannose (weight/weight); iii) an amount not greater than 0.1% levulinic acid (weight/weight); and iv) an amount not greater than 0.1% formic acid (weight/weight). In the ionic liquid stream compositions disclosed herein, the solvent S3 can be cyclohexanol.

Provided herein are glucose product stream compositions. The glucose product stream compositions comprising at least 90% monosaccharides (weight/dry solids); and at least 100 ppb of a marker molecule, wherein the marker molecule is selected from an ionic liquid cation, imidazole, an imidazole derivative, an imidazole-sugar adjuvant, hydroxymethyl furfural, or solvent S3. In the glucose product stream compositions, the glucose product stream compositions can further comprise at least 95% C6 carbohydrates (weight/dry solids). In the glucose product stream compositions disclosed herein, the glucose product stream compositions can further comprise at least 90% glucose (weight/dry solids); and at least one non-glucose C6 carbohydrate, wherein at least 90% of the non-glucose carbohydrate is mannose (weight/weight).

Provided herein are cellulose remainder pulp compositions. The cellulose remainder pulp compositions can comprise: (i) a C6 sugars to solid ratio of at least 77%; (ii) a lignin content of an amount not greater than 15%; (iii) an ash content of an amount not greater than 6%; and (iv) a C5 sugars to solid ratio of an amount not greater than 2%. In the cellulose remainder pulp compositions disclosed herein, (i) the C6 sugars to solid ratio can be at least 90%; (ii) the lignin content can be an amount not greater than 6%; and (iii) the ash content can be an amount not greater than 3%. In the cellulose remainder pulp compositions disclosed herein, (i) the C6 sugars to solid ratio can be at least 93%; (ii) the lignin content can be an amount not greater than 5%; (iii) the ash content can be an amount not greater than 1%; and (iv) the C5 sugars to solid ratio can be an amount not greater than 1%. In the cellulose remainder pulp compositions disclosed herein, (i) the C6 sugars to solid ratio is at least 96%; (ii) the lignin content can be an amount not greater than 3%; (iii) the ash content can be an amount not greater than 0.1%; and (iv) the C5 sugars to solid ratio can be an amount not greater than 0.1%.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
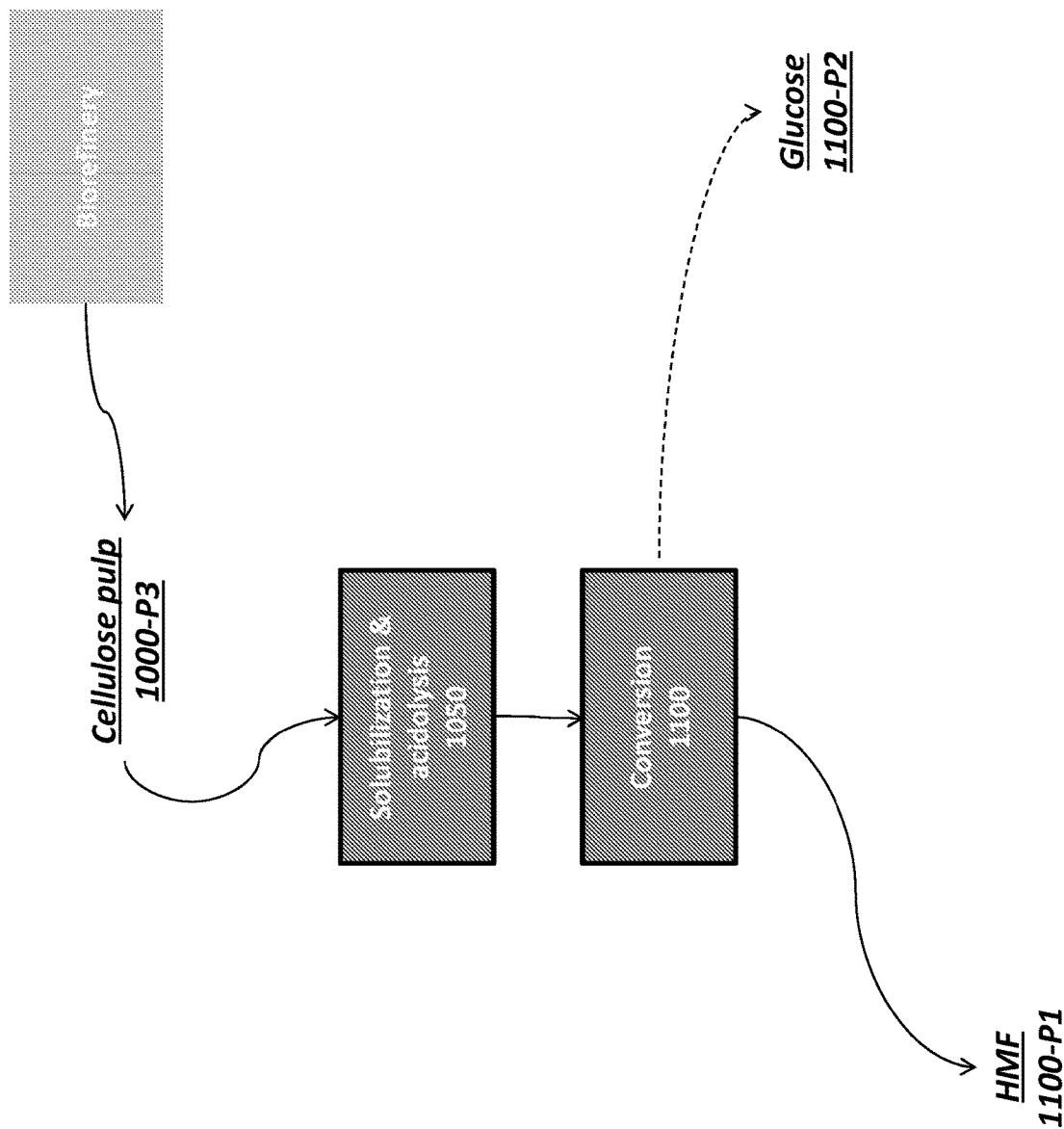
FIG. 1 illustrates a schematic diagram of exemplary conversion processes to convert biomass to hydroxymethyl furfural, with optional co-production of refined glucose.

The present disclosure provides for processes, methods, systems, and compositions for efficiently utilizing biomass for the production of hydroxymethyl furfural, di-substituted furanic derivatives, and saccharides. Hydroxymethyl furfural and di-substituted furanic derivatives are intermediates in a production chain that is based on biomass. Biomass can include lignocellulosic biomass, specifically, cellulose remainder pulp. The biomass used in the processes and methods disclosed herein is not limited to cellulose remainder pulp. Alternatives to cellulose remainder pulp include cardboard, waste cardboard, paper mill pulp, dissolving pulp, cotton fibers or linters, or paper recycling. Hydroxymethyl furfural can be recovered in a solvent that is suitable for conversion reactions of the hydroxymethyl furfural to conversion products. Hydroxymethyl furfural can be derived from cellulosic sugars, e.g., according to the conversion processes and methods (conversions) that are disclosed herein. The hydroxymethyl furfural produced according to this disclosure can be converted to many other chemical products. The disclosed conversions facilitate the production of valuable chemicals from biomass.

The production of sugars and sugar conversion products from biomass can include the use of ionic liquids (IL), as disclosed herein. Ionic liquids and deep eutectic solvents (DES) can solubilize cellulose, including crystalline cellulose. These highly charged liquids can open up the crystalline structure of crystalline cellulose to expose the saccharide polymer and can help facilitate its saccharification either by acidolysis with low concentration mineral acid (e.g., hydrochloric acid) or by enzymatic catalysis. A description of ionic liquids can also be found in U.S. Pat. Nos. 8,790,542; 9,157,130; PCT/US2013/039194; U.S. Pat. No. 6,177,575; and US 2010/0196967.

Cellulose remainder pulp can be produced through biorefining processes, such as those known in the art, and as exemplified by PCT/US2013/039585 and PCT/US2013/068824. It is desirable that an input biomass material, e.g., cellulose remainder pulp, comprise mostly cellulose and residue level of other biomass components, as described herein. Lignin, ash, hemicellulose, and extractives, which can be produced during processing of biomass to cellulose pulp, can hinder conversions, and can be efficiently removed in order to prevent build up, which can occur due to the recycling of the solvents that are used in the process.

PCT/US2013/039585 and PCT/US2013/068824 disclose processes and methods to extract hemicellulose, ash, and extractives from biomass in a first extraction process. The remaining lignocellulose material can be extracted in a second extraction process to remove lignin, leaving the remaining cellulose pulp essentially free of lignin, hemicelluloses, ash, and extractives, which results in cellulose remainder pulp. Cellulose remainder pulp can be derived from softwood, hardwood, bagasse, sugarcane leaves and stalks, annual crops, or other biomass feedstock including forest residues, pins and fines, and agricultural or industrial residues by the processes and methods described therein.

Cellulose remainder pulp can be characterized by known characterization methods. For example, cellulose remainder pulp can be characterized according to the Laboratory Analytical Procedure provided by the National Renewable Energy Laboratory in the Technical Report NREL/TP-510-42618. Briefly, the Laboratory Analytical Procedure of NREL/TP-510-42618 includes the hydrolysis of cellulose and hemicellulose polymers in sulfuric acid and determination of the dissolved sugars, from which the amount of carbohydrates in the biomass can be calculated, where lignin is determined to be the remaining solids. Examples of data obtained from cellulose remainder pulp are disclosed herein. For example, Example 1, Example 2, and Example 3 describe cellulose remainder pulp from *eucalyptus* and pine and Example 4 describes cellulose remainder pulp from bagasse.

Cellulose remainder pulp as provided herein can be characterized by one or more physical attributes.

In some instances, cellulose remainder pulp can be characterized by (i) a C6 sugars to solid ratio of at least 77% (weight/weight); (ii) a lignin content of not greater than 15% (weight/weight); (iii) an ash content of not greater than 6% (weight/weight); and (iv) a C5 sugars to solid ratio of not greater than 2% (weight/weight). In some instances, cellulose remainder pulp can be characterized by (i) a C6 sugars to solid ratio of at least 90% (weight/weight); (ii) a lignin content of not greater than 6% (weight/weight); and (iii) a ash content of not greater than 3% (weight/weight). In some instances, cellulose remainder pulp can be characterized by (i) a C6 sugars to solid ratio of at least 93% (weight/weight); (ii) a lignin content of not greater than 5% (weight/weight); (iii) an ash content of not greater than 1% (weight/weight); and (iv) a C5 sugars to solid ratio of not greater than 1% (weight/weight). In some instances, cellulose remainder pulp can be characterized by (i) a C6 sugars to solid ratio of at least 96% (weight/weight); (ii) a lignin content of not greater than 3% (weight/weight); (iii) an ash content of not greater than 0.1% (weight/weight); and (iv) a C5 sugars to solid ratio of not greater than 0.1% (weight/weight).

In some instances, cellulose remainder pulp can be characterized by (i) C6 sugars to solid ratio of at least 70% weight/weight; (ii) glucose to solid ratio of at least 70% weight/weight; (iii) C5 sugars to solid ratio of not greater than 5% weight/weight; and (iv) total sugars to solid ratio of at least 75% weight/weight. In some instances, cellulose remainder pulp can be characterized by (i) not greater than 80, 70, 60, 50, or 40% alpha cellulose weight/weight; (ii) at least 30, 40, 50, or 60% beta cellulose weight/weight; (iii) at least 0.2, 0.5, 1, or 1.5% gamma cellulose weight/weight; and (iv) not greater than 0.1% dichloromethane extractives weight/weight. In some instances, cellulose remainder pulp can be characterized by (i) average fiber length of not greater than 3, 2, 1, or 0.5 mm, (ii) mean fiber width of about 20 micrometer; and (iii) fines content of at least 10, 20, 30, 40, or 50% weight/weight.

In some instances, cellulose remainder pulp can be characterized by one or more, two or more, three or more, or four or more of the following characteristics: (i) cellulose to solid ratio of at least 80% (weight/weight); (ii) crystalline cellulose to solid ratio of at least 50% (weight/weight); (iii) lignin to solid ratio of not greater than 15% (weight/weight); and (iv) hemicellulose carbohydrate to solid ratio of not greater than 6% (weight/weight). In some instances, cellulose remainder pulp can be characterized by cellulose to solid ratio of at least 85% (weight/weight). In some instances, cellulose remainder pulp can be characterized by one or more, two or more, three or more, or four or more of the following characteristics: (i) cellulose to solid ratio of at least 85% (weight/weight); (ii) crystalline cellulose to solid ratio of at least 50% (weight/weight); (iii) lignin to solid ratio of not greater than 10% (weight/weight); and (iv) hemicellulose carbohydrate to solid ratio of not greater than 4% (weight/weight). In some instances, cellulose remainder pulp can be characterized by cellulose of at least 90% (weight/weight).

In some instances, cellulose remainder pulp can be characterized by one or more, two or more, three or more, four or more, five or more, or six or more of the following characteristics: (i) C6 sugars to solid ratio of at least 70% (weight/weight); (ii) glucose to solid ratio of at least 70% (weight/weight); (iii) C5 sugars to solid ratio of not greater than 5% (weight/weight); (iv) total sugars to solid ratio of at least 75% (weight/weight); (v) trace Mg, Mn, Na, Zn not greater than 10 ppm; and (vi) trace Cu, Fe, K, Al, Cr, of not greater than 200 ppm. In some instances, cellulose remainder pulp can be characterized by one or more, two or more, three or more, four or more, five or more, or six or more, seven or more, eight or more, nine or more, ten or more, eleven or more, or twelve or more of the following characteristics: (i) a loss of drying from 2.0 to 5.0%, or 1.5, 2.0, 2.5, 3.0, 3.5, 4.0, 4.5, or 5.0%; (ii) bulk density of from 0.29 to 0.36 g/cc, or 0.2, 0.25, 0.29, 0.3, 0.35, 0.36, or 0.4 g/cc; (iii) passes identification tests A and B in the Food Chemical Codex (FCC) ($5^{th}$ Ed. 2004), wherein in test A a white opaque, bubble-free dispersion that does not form a supernatant liquid at the surface is obtained after 100 mL of a dispersion of 45 g of cellulose in 255 mL water is mixed for 5 minutes in a high-speed power blender (18,000 rpm) that is left standing in a 100-mL graduated cylinder for 3 hours, and wherein in test B 20 mL of the dispersion is mixed with a few drops of iodine test solution and no purplish to blue or blue color is produced; (iv) degree of polymerization of not greater than 350 units; (v) a pH of from 5.5 to 7.0, or 5.0, 5.5, 6.0, 6.5, 7.0, or 7.5; (vi) conductivity not greater than 75 $\mu$S/cm; (vii) residue on ignition not greater than 0.05% (weight/weight); (viii) water soluble substances are not greater than 12.5 mg/5 g; (viii) ether soluble substances are not greater than 5.0 mg/10 g; (ix) heavy metals are not greater than 0.001% (weight/weight); (x) solubility in copper tetramine hydroxide; (xi) particle size under 250 microns is at least 10% (weight/weight); and (xii) particle size under 150 microns is at least 50% (weight/weight).

In some instances, cellulose remainder pulp can be characterized by one or more, two or more, three or more, four or more of the following characteristics: (i) cellulose to solid ratio of at least 90% (weight/weight); (ii) crystalline cellulose to solid ratio of at least 50% (weight/weight); (iii) lignin to solid ratio of not greater than 10% (weight/weight); and (iv) hemicellulose carbohydrate to solid ratio of not greater than 4% (weight/weight).

In some instances, the C6 sugars to solid ratio is not greater than 100% (weight/weight). In some instances, the C6 sugars to solid ratio is from 77 to 100% (weight/weight). In some instances, the C6 sugars to solid ratio is at least 45, 50, 55, 60, 65, 70, 75, 80, 83, 85, 90, 95, 99, or 100% (weight/weight). In some instances, the lignin content is at least 0.001% (weight/weight). In some instances, the lignin content is from 0.001 to 15% (weight/weight). In some instances, the lignin content is not greater than 15, 13, 12, 11, 10, 9, 8, 7, 6, 5, 4, 3, 2, 1, 0.5, or 0.05% (weight/weight). In some instances, the ash content is at least 0.001% (weight/weight). In some instances, the ash content is from 0.001% to 6% (weight/weight). In some instances, the ash content is not greater than 5, 4, 3, 2, 1, 0.5, or 0.05% (weight/weight). In some instances, the C5 sugars to solid ratio is at least 0.001% (weight/weight). In some instances, the C5 sugars to solid ratio is from 0.001 to 2% (weight/weight). In some instances, cellulose remainder pulp can be characterized by a C5 sugars to solid ratio of not greater than 10, 5, 4, 3, 2, 1, 0.5, or 0.05% (weight/weight).

In some instances, the glucose to solid ratio is at least 45, 50, 55, 60, 65, 70, 75, 80, 83, 85, 90, 95, or 99% (weight/weight). In some instances, the total sugars to solid ratio is at least 45, 50, 55, 60, 65, 70, 75, 80, 83, 85, 90, 91, 92, 93, 94, 95, 96, 97, 98, or 99% (weight/weight). In some instances, the residual lignin can be characterized by at least 85, 90, or 95% acid insoluble lignin (insoluble lignin weight/total lignin weight).

The amount of inorganic impurities in a cellulosic remainder pulp sample can be measured by inductively coupled plasma atomic emission spectrometry (ICP-AES). In some instances, cellulose remainder pulp can be characterized by an amount of trace sulfur not greater than 1000, 900, 800, 700, 600, 500, 400, 300, 200 or 100 ppm. In some instances, cellulose remainder pulp can be characterized by an amount of trace calcium not greater than 1000, 900, 800, 700, 600, 500, 400, 300, 200 or 100 ppm. In some instances, cellulose remainder pulp can be characterized by an amount of trace iron not greater than 1000, 900, 800, 700, 600, 500, 400, 300, 200 or 100 ppm. In some instances, cellulose remainder pulp can be characterized by an amount of trace potassium not greater than 1000, 900, 800, 700, 600, 500, 400, 300, 200, 100 or 50 ppm. In some instances, cellulose remainder pulp can be characterized by an amount of trace magnesium not greater than 500, 400, 300, 200, 100, 90, 80, 70, 60, 50, 40, 30, 20 or 10 ppm. In some instances, cellulose remainder pulp can be characterized by an amount of trace sodium not greater than 500, 400, 300, 200, 100, 90, 80, 70, 60, 50, 40, 30, 20 or 10 ppm. In some instances, cellulose remainder pulp can be characterized by amount of trace chromium not greater than 500, 400, 300, 200, 100, 90, 80, 70, 60, 50, 40, 30, 20 or 10 ppm. In some instances, cellulose remainder pulp can be characterized by not greater than 10 ppm of Mg, Mn, Na, and Zn, and the amount of trace Cu, Fe, K, Al, and Cr is not greater than 200 ppm.

In some instances, cellulose remainder pulp can be characterized by cellulose of at least 80, 85, 90, 92, 94, 96, 98, or 99%. The loss of drying can be percent of material lost weight/weight when the cellulose remainder pulp is dried from a solid to dry solid. The cellulose remainder pulp can be heated for a period of time to dry. The cellulose remainder pulp can be heated to a temperature not greater than 200, 190, 180, 170, 160, 150, 140, 130, 120, 110, 100, 90, 80, 70, 60, 50, 40, or 30° C. for the period of time to dry. The period of time the cellulose remainder pulp is heated to dry can be not greater than 100, 90, 80, 70, 60, 50, 48, 40, 30, 24, 20, 16, 12, 10, 9, 8, 7, 6, 5, 4, 3, 2, 1, or 0.5 hours.

In some instances, cellulose remainder pulp can be characterized by a high cellulose to solid ratio, a low lignin to solid ratio, and a low hemicellulose carbohydrate to solid ratio. In some aspects, the cellulose compositions are characterized by a high crystalline cellulose to solid ratio. In some aspects, the cellulose compositions are characterized by a high cellulose to solid ratio, a low lignin to solid ratio, a high crystalline cellulose to solid ratio, and a low hemicellulose carbohydrate to solid ratio. In some instances, cellulose remainder pulp can be characterized by cellulose to solid ratio of at least 90, 92, 94, 96, 98, or 99% (weight/weight). In some instances, cellulose remainder pulp can be characterized by crystalline cellulose to solid ratio of at least 50, 60, 70, 80, 90% (weight/weight). In some instances, cellulose remainder pulp can be characterized by lignin to solid ratio of not greater than 10, 9, 8, 7, 6, 5, 4, 3, 2, or 1% (weight/weight). In some instances, cellulose remainder pulp can be characterized by hemicellulose carbohydrate to solid ratio of not greater than 4, 3, 2, or 1% (weight/weight).

Figure 2:
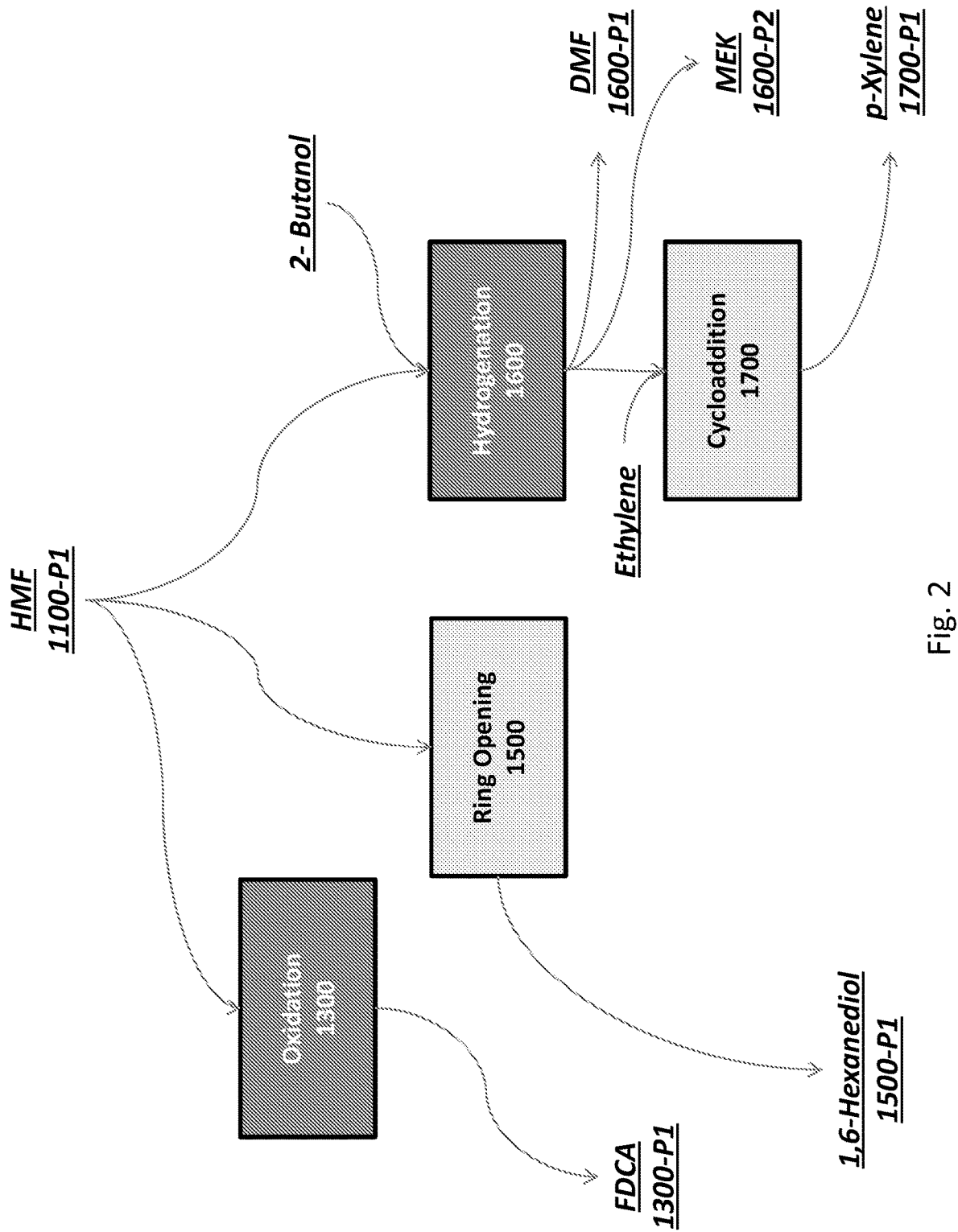
FIG. 2 illustrates a schematic diagram of exemplary sequential conversion processes to convert hydroxymethyl furfural to various conversion products.
Figure 3:
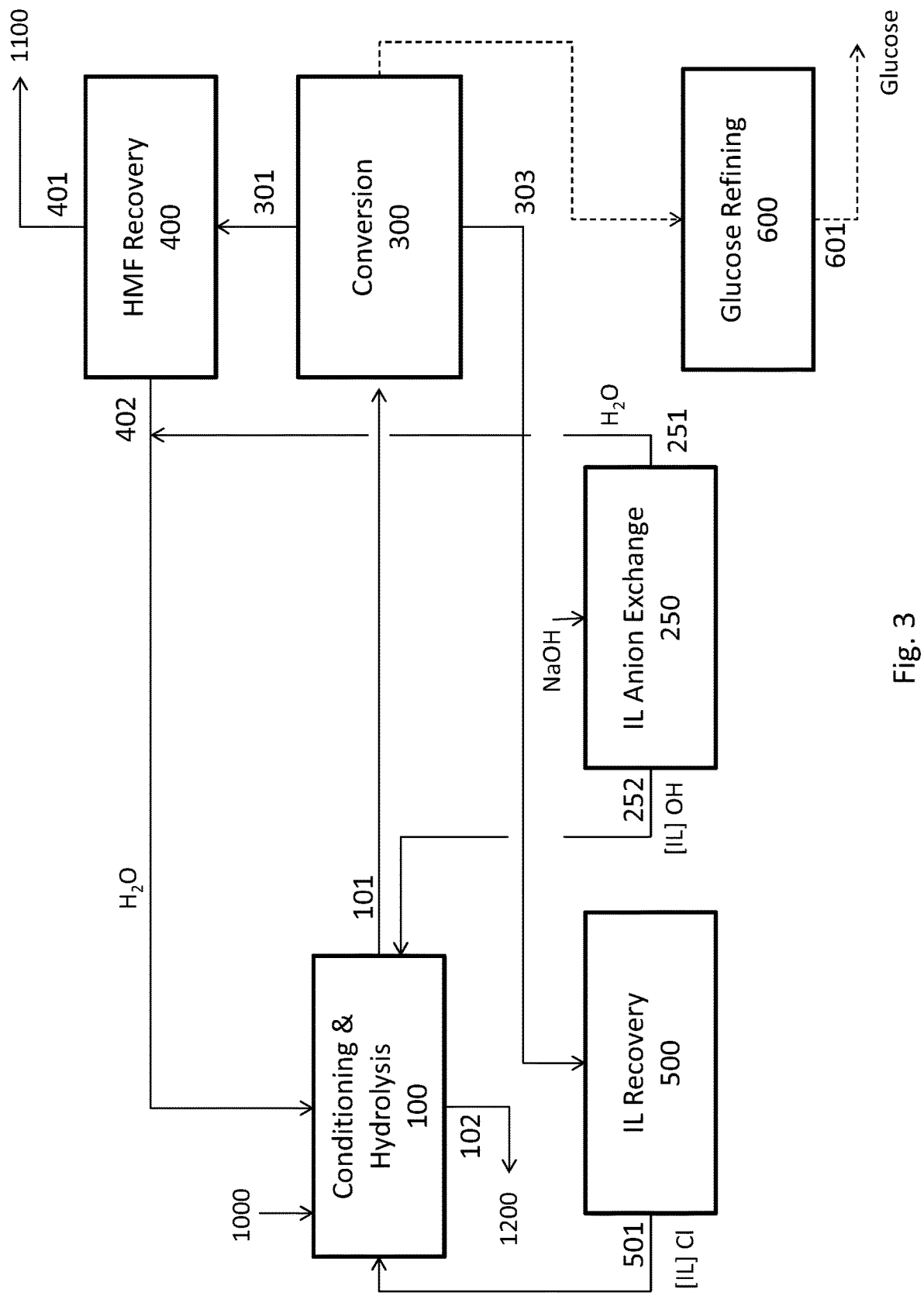
FIG. 3 illustrates a schematic diagram of an exemplary process to convert cellulose pulp to hydroxymethyl furfural with recovery of ionic liquid and with optional co-production of refined glucose. The process is further detailed in FIG. 4, FIG. 5, FIG. 6, FIG. 7, and FIG. 8.

An overview of exemplary cellulose pulp sequential hydrolysis, isomerization, and dehydration to hydroxymethyl furfural according to embodiments disclosed herein is provided in FIG. 1, FIG. 2, and FIG. 3. As provided in FIG. 1, (1) cellulose pulp 1000 is extracted and refined from biomass in a biorefinery; (2) cellulose pulp 1000 is solubilized in ionic liquid and saccharified by acidolysis 1050; (3) the resulting ionic liquid solution comprising monosaccharides, oligosaccharides, and polymeric saccharides is subjected to conversion 1100 thereby producing hydroxymethyl furfural 1100-P1 and optionally glucose 1100-P2. As provided in FIG. 2, (4) hydroxymethyl furfural is further converted to conversion products, including: (4)(i) oxidation 1300 of hydroxymethyl furfural to 2,5-furandicarboxylic acid (FDCA) 1300-P1; (4)(ii) hydrogenation 1600 of hydroxymethyl furfural with 2-butanol as hydrogen donor to form 2,5-dimethylfuran (DMF) 1600-P1 and methyl ethyl ketone (MEK) 1600-P2; (5) cycloaddition 1700 of 2,5-dimethylfuran with ethylene to form p-xylene 1700-P1; or (4)(iii) conversion of 2,5-dimethylfuran through a ring opening reaction 1500 to 1,6-hexanediol 1500-P1. Steps (1), (2), (3), and (4)(i) can be performed consecutively without isolation of intermediate products. Steps (1), (2), (3), and (4)(ii) can be performed consecutively without isolation of intermediate products. Steps (1), (2), (3), (4)(ii), and (5) can be performed consecutively without isolation of intermediate products. Steps (1), (2), (3), and (4)(iii) can be performed consecutively without isolation of intermediate products.

FIG. 3 provides a schematic description of stepwise processes for the production of hydroxymethyl furfural from cellulose pulp. Cellulose pulp 1000 can be first conditioned in conditioning unit 100 in the ionic liquid to provide solubilized cellulose. Hydrochloric acid and water can be added to promote hydrolysis so as to provide a solution of monosaccarides, disaccharides, and hydroxymethyl furfural in the ionic liquid. Base and water can be added to neutralize the solution 251, and humins and residual lignin can be separated out. The base can be the hydroxide form of the ionic liquid 252. The hydroxide form of the ionic liquid 252 can be produced in the ionic liquid anion exchanger 250, thus reducing the amount of salt formed in the process. For example, sodium ions can be present in an amount not greater than 0.5, 1, 1.5, 2, 2.5, 3, 3.5, 4, 4.5, 5, or 5.5%. Stream 101 of de-acidified solution comprising saccharides, hydroxymethyl furfural, organic acids, water, and ionic liquid can be the feed for the conversion process 300. Stream 101 can be separated by chromatography to yield: (i) an aqueous stream 301 comprising hydroxymethyl furfural and organic acids; (ii) an ionic liquid/aqueous stream 302 comprising monosaccharides; and (iii) an ionic liquid/aqueous stream 303 comprising disaccharides. As further detailed below and provided in FIG. 5 and FIG. 6, stream 302, comprising monosaccharides, can be recycled through isomerization 330 and dehydration 350 stages.

Stream 301 can be transferred to hydroxymethyl furfural recovery process 400, where water can be removed and hydroxymethyl furfural can be separated from organic acids and water and isolated as a solution in a solvent suitable for further downstream conversions. Stream 303 can be transferred to ionic liquid recovery 500, where water can be removed by evaporation, azeotropic evaporation, or adsorption, alternatively or in combination. Cellobiose can be fractionated with the ionic liquid, and can be returned for further hydrolysis and sequential conversion. As further detailed below and presented in FIG. 6, stream 302 comprising monosaccharides can be separated in a second chromatography separation 315 to yield: (i) an aqueous stream 316 comprising glucose and (ii) an ionic liquid/aqueous stream 317 comprising glucose. Stream 317 can be recycled through isomerization 330 and dehydration 350 stages. Stream 316 can be transferred to glucose recovery and refining, where glucose can be recovered and refined by at least one of the methods comprising evaporation, contact with a strong acid cation (SAC) resin, an anion exchanger, a mixed bed (MB) resin, or activated carbon (AC). Each of these is described in further detail herein.

Where a range of numerical values is recited herein, unless otherwise stated, the range is intended to include the endpoints thereof, and all integers and fractions within the range. It is not intended that the scope of the invention be limited to the specific values recited when defining a range. All values specified herein can be "about" that value or exactly that value, where the term "about" refers to variation in the reported numerical quantity that can occur. The term "about" means within 10, 9, 8, 7, 6, 5, 4, 3, 2, or 1% of the reported numerical value.

As used herein, the term "sugars" and "saccharides" is used interchangeably.

As used herein, the terms "comprises," "comprising," "includes," "including," "has," "having," "contains," or "containing," or any other variation thereof, are intended to cover a non-exclusive inclusion. As used herein, the term "consisting of" is intended to cover an exclusive inclusion. As used herein, the term "consisting essentially of" is intended to cover an exclusion limited to materials, steps, or components that do not materially affect the basic novel characteristics of the claimed matter. As used herein, the term "comprising" encompasses the terms "comprising," "consisting essentially of," and "consisting of." For example, a composition, a mixture, process, method, article, or apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or.

I. Cellulose Pulp Solubilization & Hydrolysis
a) Cellulose Pulp Solubilization

Figure 4:
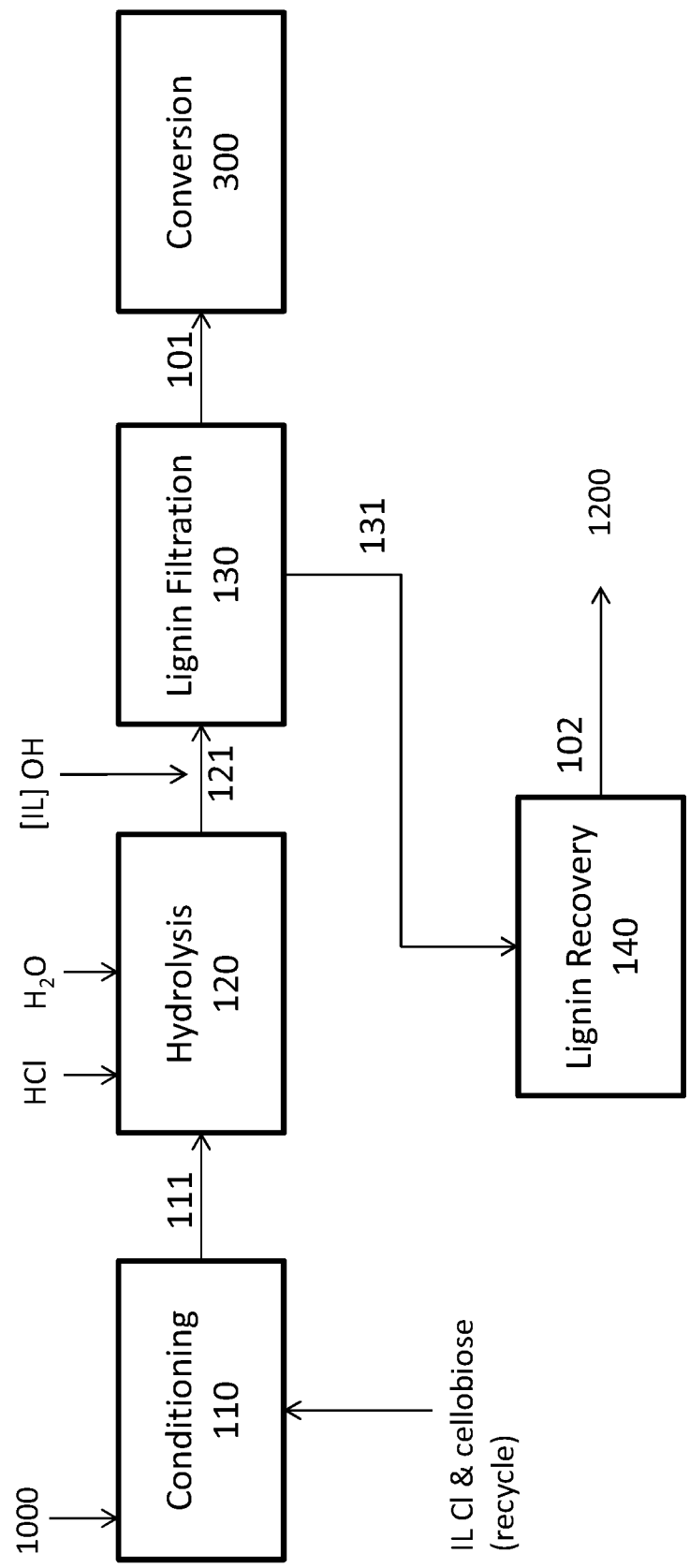
FIG. 4 illustrates a schematic diagram of an exemplary process for the hydrolysis of cellulose pulp to monosaccharides in ionic liquid medium and for the removal and recovery of residual lignin.

A schematic of exemplary processes for solubilizing cellulose pulp and hydrolyzing it to glucose is provided in FIG. 4. Cellulose pulp 1000 can be conditioned 110 in a suitable liquid to solubilize it and open up the crystalline structure of cellulose, making it accessible for hydrolysis. The conditioning can be conducted by stirring the pulp and the liquid at controlled time and temperature. A suitable liquid can be selected from ionic liquids or deep eutectic solvents. The suitable liquid can comprise recycled ionic liquid comprising cellobiose. The recycled ionic liquid stream can be treated to remove excess water and impurities as described in further detail herein. Such recycling can allow for further hydrolysis of unreacted cellobiose from earlier reaction cycles, thus maximizing overall hydroxymethyl furfural yield from cellulose. Optionally, stream 111 can be transferred to another reaction vessel to conduct hydrolysis 120. Alternatively or in combination, hydrolysis 120 can be conducted in the same vessel as hydrolysis step 100 (see FIG. 3). Hydrolysis 120 can be initiated by the addition of acid and water to stream 111. After hydrolysis is complete, the pH can be increased, e.g., by ionic liquid in the hydroxide form, and water can be added to stream 121 to cause precipitation of lignin residues that are co-dissolved while cellulose can be solubilized, the lignin can be filtered in 130, and the lignin filtered stream 131 can be recovered and refined in 140, in order to collect high purity lignin 1200. The pH increase can be affected by the addition of the basic form of the ionic liquid used as solvent. Additional filtration to remove humins can be conducted prior to altering the pH.

Cellulose pulp can be solubilized in ionic liquid or in deep eutectic solvent by admixing the pulp in the molten salt solution at a temperature above the melting point of the ionic liquid or the deep eutectic solvent. At least 5, 10, 15, 20, or 25 weight/weight cellulose pulp can be added to the molten ionic liquid or deep eutectic solvent, and is mixed at a temperature from 100 to 150° C. for at least 30, 45, 60, 90, 120 180, 240, 300, or 360 minutes.

Cellulose pulp can be pretreated prior to solubilizing in ionic liquid to remove residual amounts of lignin or ash. Residual lignin can comprise at least 85, 90, 95, or 99% acid insoluble lignin weight/total lignin weight. Any process suitable to further remove such impurities can be applied, including but not limited to, washing with water or basic solution or acidic solution, bleaching by any oxidizing agent, or washing with a solvent solution.

Ionic liquids are salts that are liquids rather than crystals at room temperatures. Numerous ionic liquids can be used in the pretreatment processes of the present disclosure. The ionic liquid can be suitable for pretreatment of the biomass and for the hydrolysis of cellulose by thermostable cellulase. Non-limiting examples of suitable ionic liquids are taught in ChemFiles (2006) 6(9) (Which are commercially available from Sigma-Aldrich; Milwaukee, Wis.). Suitable ionic liquids include, but are not limited to, 1-alkyl-3-alkylimidazolium alkanate, 1-alkyl-3-alkylimidazolium alkyl sulfate, 1-alkyl-3-alkylimidazolium methyl sulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising 1, 2, 3, 4, 5, 6, 7, 8, 9, or 10 carbon atoms, and an "alkanate" is an alkanate comprising 1, 2, 3, 4, 5, 6, 7, 8, 9, or 10 carbon atoms. The "alkyl" can be an alkyl group comprising 1, 2, 3, or 4 carbon atoms. The "alkyl" can be a methyl group, ethyl group, or butyl group. The "alkanate" can be an alkanate comprising 1, 2, 3, or 4 carbon atoms. The "alkanate" can be an acetate. The halide can be chloride.

Ionic liquid can comprise 1-ethyl-3-methylimidazolium acetate (EMIM acetate), 1-ethyl-3-methylimidazolium chloride (EMIM Cl), 1-ethyl-3-methylimidazolium hydrogensulfate (EMIM $HOSO_3$), 1-ethyl-r-methylimidazolium methylsufate (EMIM $MeOSO_3$), 1-ethyl-3-methylimidazolium ethylsulfate (EMIM $EtOSO_3$), 1-ethyl-3-methylimidazolium methanesulfonate (EMIM $MeSO_3$), 1-ethyl-3-methylimidazolium tetrachloroalumnate (EMIM $AlCl_4$), 1-ethyl-3-methlimidazolium thiocyanate (EMIM SCN), 1-butyl-3- methylimidazolium chloride (BMIM Cl), 1-butyl-3-methylimidazolium hydrogensulfate (BMIM HOSO$_3$), 1-butyl-3-methylimidazolium acetate (BMIM MeSO$_3$), 1-butyl-3-methylimidazolium methyl sulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethyl sulfate (EDIM EtOSO$_3$), Tris(2-hydroxyethyl)methylammonium methyl sulfate (MTEOA MeOSO$_3$), 1-methylimidazolium chloride (MIM Cl), 1-methylimidazolium hydrogensulfate (MIM HOSO$_3$), 1,2,4-trimethylpyrazolium methyl sulfate, tributylmethylammonium methyl sulfate, choline acetate, choline salicylate, and the like.

Ionic liquid can comprise chloride ionic liquid. Ionic liquid can be an imidazolium salt. Ionic liquid can be a 1-alkyl-3-imidazolium chloride, such as 1-ethyl-3-methylimidazolium chloride or 1-butyl-3-methlimidazolium chloride.

Ionic liquid can comprise pyridinium salts, pyridazinium salts, pyrimidinium salts, pyrazinium salts, imidazolium salts, pyrazolium salts, oxazolium salts, 1,2,3-triazolium salts, 1,2,4-triazolium salts, thiazolium salts, isoquinolium salts, quinolinium salts, isoquinolinium salts, piperidinium salts, and pyrrolidinium salts. Exemplary anions of the ionic liquid include, but are not limited to, halogens (e.g., chloride, fluoride, bromide, and iodide), pseudoholgens (e.g., azide and isocyanate), alkyl carboxylate, sulfonate, acetate, and alkyl phosphate.

Ionic liquid can be selected such that it is a weak Lewis acid when in chloride form, and weak Lewis base in its hydroxide form.

Ionic liquid can comprise one compound or a mixture of compounds.

Contacting a cellulose pulp material with an ionic liquid can be performed at a temperature from 100 to 160° C. For example, at a temperature of 100, 110, 120, 130, 140, 150, or 160° C. Contacting with an ionic liquid step can be performed for a period from 0.5 hour to 16 hours, or from a period from 1 hour to 12 hours, or from a period from 1 hour to 6 hours.

Cellulose pulp can be dissolved in a deep eutectic solvent comprising choline chloride-citric acid-citric acid monohydrate system. The choline chloride-citric acid-citric acid monohydrate system that can be used for the dissolution can be prepared by mixing choline chloride, citric acid and citric acid monohydrate in a ratio of 4:1:1 (by weight) at 85 to 95° C.

b) Acid Hydrolysis

Hydrolysis can be conducted by addition of acid as catalyst for the hydrolysis of the solubilized cellulose. The temperature of the ionic liquid solution comprising solubilized cellulose can be adjusted before the addition of the acid catalyst. This adjustment can comprise cooling the solution to 100, 105, 110, or 115° C.

An acid catalyst can comprise an aqueous acidic solution. Aqueous acidic solutions include, but are not limited to, hydrochloric acid solutions, sulfuric acid solutions, and mixtures thereof. The aqueous acidic solution can be a hydrochloric acid solution. The aqueous acidic solution can have a concentration from 2.0M to 12 M. The aqueous acidic solution can have a concentration of acid of not greater than 12, 11, 10, 9, 8, 7, 6, 5, 4, 3, or 2M. The aqueous acidic solution can have a concentration of acid of not greater than 2M. An aqueous acidic solution having a concentration from 2.0 M to 12 M can be added to a solution of cellulose pulp material in ionic liquid. An aqueous acidic solution having a concentration from 2.0 M to 12 M can be formed by adding an aqueous acidic solution having a concentration of at least 2.0 M to 12 M and water independently to the solution of the cellulose pulp material in the ionic liquid to obtain an aqueous solution having a concentration from 2.0 M to 12 M. An aqueous acidic solution having a concentration of at least 2.0 M to 12 M and water can be added to the solution of the cellulose pulp material in the ionic liquid by aliquot. An aqueous acidic solution having a concentration of at least 2.0 M to 12 M and water can be continuously added to the solution of cellulose pulp in the ionic liquid via a pump or other means for continuous addition.

Adding an aqueous acidic solution to the solution comprising the cellulose pulp material in the ionic liquid can be performed at a temperature from 60 to 110° C. The adding step can be performed for a period of time from 0.5 to 6 hours.

Acid concentration in the ionic liquid solution can be maintained by gradually adding suitable amounts of acid and water over the course of the reaction. An aqueous acidic solution having a concentration from 2.0 M to 12 M can be added to the solution of the cellulose pulp material in the ionic liquid. Aqueous acid solution can be added in one dose or stepwise. Aqueous acidic solution can be continuously added to the solution of cellulose pulp in the ionic liquid via a pump or other means for continuous addition.

Adding an aqueous acidic solution to the solution of the cellulose pulp material in the ionic liquid can be performed at a temperature of from 80 to 140° C.

The ionic liquid solution at the end of hydrolysis can comprise glucose weight yield of at least 50% of the starting cellulose, cellobiose weight yield of at least 5% of the starting cellulose, and hydroxymethyl furfural weight yield to at least 1% of the starting cellulose. Such solutions are described in U.S. Pat. No. 8,722,878 or WO 2013/166237. It should be noted that a 100% molar yield of hydrolyzing cellulose to glucose is equivalent to 110% weight yield. The ionic liquid solution can comprise at least 50, 60, 70, 80, 90, or 95% weight yield of glucose from the starting cellulose. At the end of the hydrolysis reaction, the dissolved solids in the ionic liquid phase can comprise at least 94% glucose, at least from 5 to 10% cellobiose, at least from 7 to 12% hydroxymethyl furfural, not greater than 1.5% levulinic acid, and not greater than 1.5% formic acid (all % weight/weight dry solids). The mass balance of the products cellulose, cellobiose, hydroxymethyl furfural, levulinic acid, and formic acid, as quantified by sampling the reaction mixture, diluting tenfold with water, filtering, and injection to a HPLC on Aminex HPX-87H column. Where the theoretical weight yield is 110%, the measured weight yield can be at least 105, 107, 109, or 110% weight yield. The high mass balance of analytes accounted for can indicate there are no significant losses of cellulose to byproducts other than the amounts detected of levulinic and formic acid. The solution can comprise a small amount of humins. The solution can be filtered through any type of suitable filter to capture and remove the humins that are present as solid particles.

Cellulose pulp can comprise lignin residue, thus this lignin can be present in the ionic liquid solution either dissolved or semi dissolved. It can be desirable to remove such lignin from the solution. The ionic liquid solution can be diluted with water at a ratio of 1:1 to 4:1, and the pH can be adjusted from 3.3 to 4, or to 3.5, by addition of the hydroxide form of the ionic liquid. For example, if the ionic liquid used as solvent is 1-ethyl-3-methylimidazolium chloride then 1-ethyl-3-methylimidazolium hydroxide is added; if the ionic liquid used as solvent is 1-butyl-3-methylimidazolium chloride, then 1-butyl-3-methylimidazolium hydroxide is added, and so on. After pH adjustment and dilution with water, lignin can be precipitated and can be filtered out by any suitable filtration unit. The filtrate can be washed with an 80:20 solution of methyl ethyl ketone and water, causing the dissolution of the precipitate into the methyl ethyl ketone phase. The solution can be contacted with strong acid cation exchanger to capture all residual ionic liquid cation on the resin. The dissolved lignin can then be recovered as disclosed in PCT/US2013/039585 and PCT/US2013/068824.

Ionic liquid can be converted to its basic form by contacting an aqueous solution of the ionic liquid with a strong base resin in the hydroxide form. Suitable commercial SBA resins can be purchased from Finex (AS 510 GC Type I, Strong Base Anion, gel form). Similar grades can be purchased from other manufacturers including Lanxess A G, Purolite, Dow Chemicals Ltd. (or Rohm & Haas, a Dow Chemicals company). Macroporous SBA resins can be used alternatively or in combination. The resin can be regenerated to the hydroxide form by periodical contacting with a sodium hydroxide solution. This conversion of ionic liquid to its basic form can provide all of the needed base for pH control of different process steps, thus eliminating the need to introduce sodium hydroxide or other bases that would form salt in the ionic liquid cycle. This can be advantageous as salt formed in the ionic liquid cycle will build up and could present a great challenge to remove from the cycle.

II. Conversion of the Hydrolysate to Hydroxymethyl Furfural

The conversion processes of cellulose hydrolysate to hydroxymethyl furfural as described herein can produce hydroxymethyl furfural at high yield. The hydrolysate can comprise ionic liquid in chloride, ionic liquid in hydroxide form, glucose, cellobiose, hydroxymethyl furfural, organic acids, and water. The conversion processes can comprise at least three process steps conducted in coordination to achieve the target high yields of hydroxymethyl furfural. Theoretically, the maximum weight yield of hydroxymethyl furfural is 77.7% weight/weight cellulose, equivalent to 100% molar yield (carbon yield). The conversion processes disclosed herein can provide an overall yield of hydroxymethyl furfural from cellulose that is at least 55, 60, 62, 64, 66, or 68% weight/weight. An example of the overall conversion processes is schematically presented in FIG. 5. The hydrolysate to hydroxymethyl furfural conversion processes can comprise at least the following steps: (1) chromatographic separation 310; (2) isomerization 330; and (3) dehydration 350. The conversion processes can comprise additional steps including, but not limited to, filtration, pH adjustment, temperature controlling, heating or cooling, evaporation, or dilution.

a) Chromatographic Separation

Figure 6:
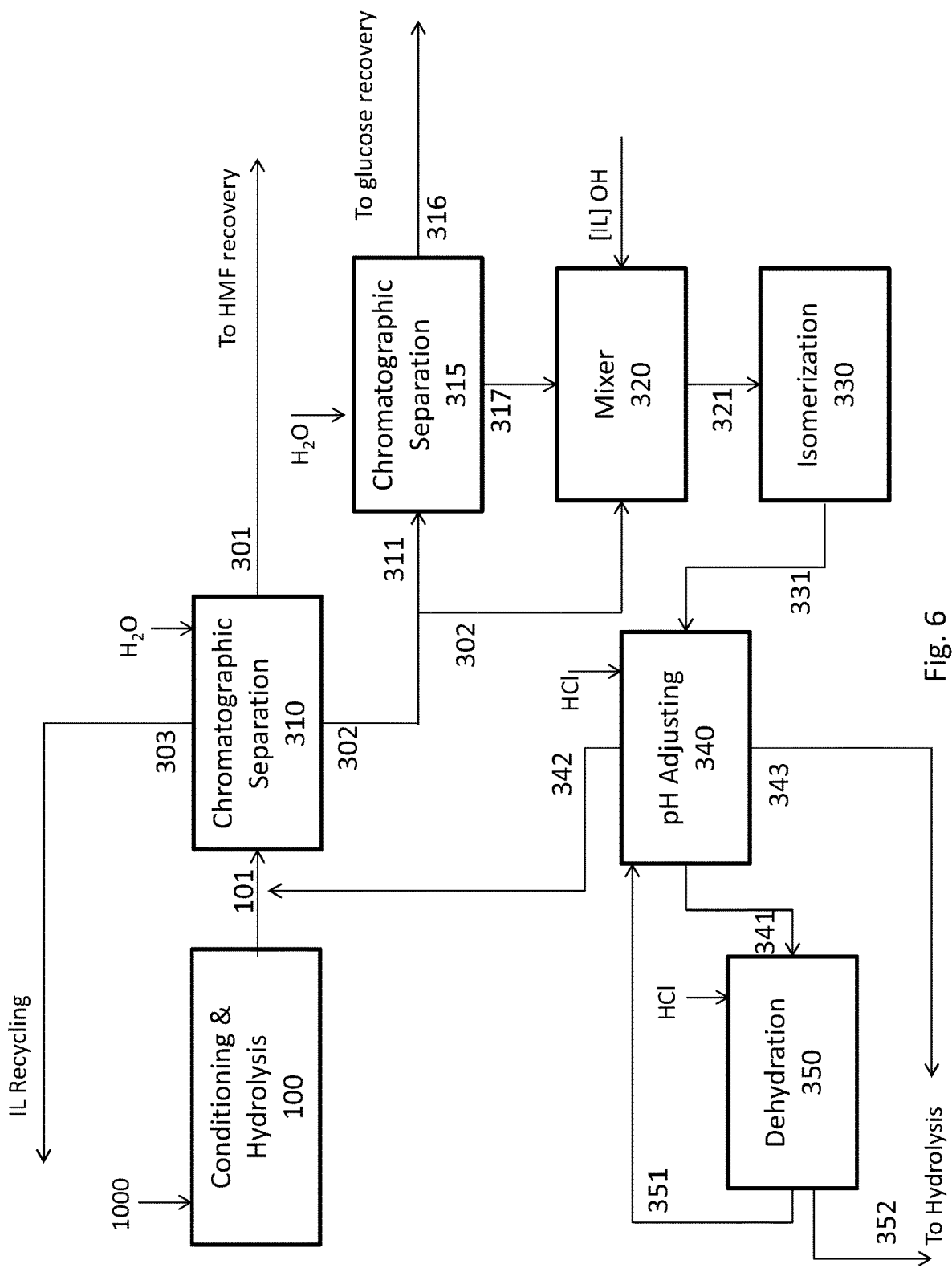
FIG. 6 illustrates a schematic diagram of an exemplary conversion process by chromatography separation, isomerization, and dehydration stages, with optional separation of glucose in addition to separation of hydroxymethyl furfural.

As provided in FIG. 6, the de-acidified stream 251 (see FIG. 3), comprising cellobiose, glucose, hydroxymethyl furfural, and organic acids, as well as water and ionic liquid, can be the fed to chromatographic separation 310. The concentration of glucose can be at least 6, 7, 8, 9, or 10%, the concentration of cellobiose can be not greater than 1%, the concentration of hydroxymethyl furfural can be not greater than 3%, the concentration of levulinic acid and formic acid can be not greater than 1.5, 1, 0.1, 0.05% each, and the concentration of water can be from 20 to 30% (all weight/weight). The concentration of glucose can be from 2 to 5%, the concentration of cellobiose can be not greater than 1%, the concentration of hydroxymethyl furfural can be not greater than 2%, the concentration of levulinic acid can be not greater than 0.1%, the concentration of formic acid can be not greater than 0.1%, the concentration of water can be not greater than 70% (all weight/weight).

The chromatography step can separate the feed mixture, stream 251, into three streams: stream 301 comprising hydroxymethyl furfural, the organic acids, and water; stream 302 comprising glucose, other saccharides, and ionic liquid; and stream 303 comprising cellobiose and ionic liquid. This separation can be achieved by selecting a suitable resin having differential affinity to the different compounds in the feed mixture, and applying a suitable sequence of steps in a simulated moving bed apparatus. A description of simulated moving bed (SMB) chromatography comprising 1-ethyl-3-methylimidazolium chloride, 1-butyl-3-methylimidazolium chloride, and 1-ethyl-3-methylimidazolium acetate is described by Caes (Chapter 6 in Catalytic Systems for Carbohydrate Conversion, B. R. Caes, Under the supervision of R. T. Raines, PhD Thesis at the University of Wisconsin—Madison and N. L. Mai et. al, Journal of Chromatography A, 1227 (2012) 67-72). Non-limiting examples of separation of hydroxymethyl furfural from ionic liquid by simulated moving bed are described herein.

Two methods for large-scale chromatographic separations are sequential simulated moving bed chromatography (SSMB) and simulated moving bed chromatography. Both methods can use a number of columns packed with a suitable sorbent and connected in series. There can be inlet ports for feed and solvent (which can include recycled solvent), and outlet ports for two or more products (or other separated fractions). The injection of the mixture solution to be separated can be periodically switched between the columns along the direction of the liquid flow, thereby simulating continuous motion of the sorbent relative to the ports and to the liquid. The simulated moving bed can be a continuous counter current type operation. Sequential simulated moving bed chromatography can be considered a more advanced method, which is a sequential type operation. Its advantages over simulated moving bed chromatography and over other, older methods can include fewer number of columns needed in the sequential simulated moving bed method as compared to the simulated moving bed method. This can require less resin, which can lower the associated cost of installation for a large system. Additionally, the pressure profile of sequential simulated moving bed chromatography can be better controlled than the pressure profile of other separation techniques, which can facilitate the use of more sensitive resins. Additionally, the achievable recovery yields and/or purity can be higher when using a sequential simulated moving bed system than obtained with simulated moving bed systems.

Fractionation of hydroxymethyl furfural and sugars from the mixture can be achieved using a strong acid cation exchanger. Suitable commercial strong acid cation resins can be purchased from Purolite (Purolite PCR 642 H, Purolite PCR 450 Na, Purolite SSTPCR 541 Ca, Purolite PCR 145 Na) or from Dow Chemicals Ltd (Dowex® 50WX4, proton form, or Dowex 99 Ca/320, $Ca^{2+}$ form), similar grades can be purchased from other manufacturers including Lanxess AG, or Finex. The strong acid cation resin can be 300 micron+/−75 in size. The strong acid cation resin can be graded chromatographic resin. The form of the resin can be exchanged to the ionic liquid cation, e.g., to the 1-ethyl-3-methylimidazolium cation or 1-butyl-3-methylimidazolium cation form, by first conditioning the resin with at least 6, 7, 8, 9, or 10 bed volumes of the respective ionic liquid in water. The pH of the feed stream 251 can be adjusted to from pH 3 to 6, by the addition of ionic liquid in the hydroxide form.

b) Isomerization

Fructose can be converted to hydroxymethyl furfural with higher selectivity and conversion at a given temperature than glucose can be converted to hydroxymethyl furfural. Therefore, to achieve high overall yield of hydroxymethyl furfural from cellulose, it can be advantageous to accelerate the isomerization of glucose to fructose. Isomerization of glucose to fructose can be catalyzed by dissolved or heterogeneous bases (for an isomerization reaction incorporated herein by reference, see: A. J. Seusabaugh Jr., P. L. Carey, CIM., 1967, 24; U.S. Pat. No. 3,684,574). Surprisingly, it was found that the isomerization of glucose to fructose can be catalyzed by increasing the pH of the water/ionic liquid solution by adding controlled amounts of ionic liquid in the hydroxide form. As provided in FIG. 5, stream 302, coming out of the chromatographic separation 310 and comprising glucose, water, and ionic liquid and having a pH of not greater than 7, can be mixed in mixer 320 with a stream comprising ionic liquid in the hydroxide form and water in order to increase the pH of the solution to at least 8, 9, 10, 11, 12, or 13. Prior to the pH adjustment, stream 302 can be concentrated by evaporation of water to a designated concentration. The resulting stream 321 can be transferred to isomerization reactor 330, where it can be stirred for from 0.5 to 10 hours, or from 5 to 7 hours, or 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 hours, at temperature of from 45 to 80° C., or from 50 to 60° C., or 40, 45, 50, 55, 60, 65, 70, 75, 80° C. Stream 321 can comprise from 1 to 10%, or 1, 2, 3, 4, 5, 6, 7, 8, 9, or 10% (weight/weight) glucose; from 17 to 25%, or 17, 18, 19, 20, 21, 22, 23, 24, or 25% (weight/weight) ionic liquid in the chloride form; and from 0.1 to 15%, or 0.1, 0.5, 1, 3, 5, 7, 10, or 15% (weight/weight) ionic liquid in the hydroxide form. The conversion of glucose to fructose under such conditions can be greater than from 20 to 30%, or 20, 25, 27, 29, or 30% (weight/weight), at selectivity greater than from 70 to 85%, or 70, 75, 80, or 85%. A major byproduct of the isomerization is mannose, forming at selectivity of from 8 to 13%, or 8, 9, 10, 11, 12, or 13% relative to glucose.

Any glucose source can be used as an alternative source for the isomerization under the same conditions. A glucose source can be commercial dextrose syrups originating from biomass, such as corn, maize, potatoes, wheat, barley, rice, and cassava, as well as alternative lignocellulosic sources. Alternative lignocellulosic sources can be hydrolyzed by other hydrolysis methods and refined to a similar level of purity as the glucose stream that results from the hydrolysis method disclosed herein, i.e. sufficient removal of hemicellulosic saccharides, lignin, ash, organic acids, extractives and other biomass associated compounds other than glucose.

c) Dehydration

The dehydration of fructose to hydroxymethyl furfural can be conducted in the water/ionic liquid solution in the presence of strong acid cation resin. A mixture comprising both fructose and glucose can be subjected to a chemical reaction wherein at least a portion of the fructose is converted to hydroxymethyl furfural and at least a portion of the glucose is not converted. At least from 50 to 99%, or 50, 55, 60, 65, 70, 75, 80, 85, 89, 90, 95, 97, or 99% of the fructose can be converted to hydroxymethyl furfural and at least from 60 to 99%, or 60, 65, 70, 75, 80, 85, 90, 95, 97, or 99% of the glucose is not converted. A macroporous strong acid cation resin can be used.

Macroporous strong acid cation resins are commercially available from several suppliers, for example Purolite PCR145K SAC Macroporous—C145 Type, Special Grading, Purolite NRW1600, Rohm and Haas Amberlite 200, Amberlite 252 and Amberlite FPC23 as well as other suppliers. At least some of the strong acid cation resin can be in the ionic liquid cation form. The resin can be regenerated periodically to at least some ionic liquid cation form to allow continuous performance. Fructose can be dehydrated to hydroxymethyl furfural while glucose is not reacted to undesired byproducts.

Prior to dehydration, the pH of the solution can be adjusted by pH adjusting 340 to acidic by contacting the solution with a weak acid cation (WAC) resin in the proton form. This contacting can also result in at least partial change of the resin to the ionic liquid cation form, as the ionic liquid cation exchanges with protons released by the resin. The pH of stream 341 can be lowered further by direct addition of an acid. The acid can be selected to be the same as the anion part of the ionic liquid, e.g., when 1-ethyl-3-methylimidazolium chloride or 1-butyl-3-methylimidazolium chloride is the ionic liquid used, the acid can be hydrochloric acid. Adjustment of pH by pH adjusting 340 allows for recycling of ionic liquid and reducing by at least from 30 to 60, or 30, 40, 50, or 60% the overall acid consumption of the process because the resin used in pH adjusting 340 can be generated back to the proton form in a later process stream, which is described further below.

The amount of water in stream 341 can be controlled by evaporation of water or addition of water. The adjusted stream 341 can be transferred to dehydration 350 to be dehydrated. Stream 341 can comprise from 4 to 10% glucose, from 1 to 4% fructose, from 15 to 45% water (all weight/weight). Dehydration 350 can comprise from 5 to 15% (weight/weight) macroporous strong acid cation resin at start of the dehydration reaction. The solution can be stirred at from 50 to 100, from 70 to 90, from 75 to 85, or 50, 55, 60, 65, 70, 75, 80, 85, 90, 95, or 100° C. for from 30 to 180, from 70 to 120, or from 80 to 100 minutes to achieve at least from 85 to 98% or 85, 90, 95, 96, 97, or 98% conversion of fructose, at least from 75 to 99%, or 75, 80, 85, 90, 95, 96, 97, 98, or 99% selectivity to hydroxymethyl furfural. Additional amounts of acid can be added to the dehydration reactor. The conversion of glucose under the same conditions can be not greater than 5, 4, 3, 2, or 1%, and the total sugar accounted for in mass balance can be at least 90, 92, 94, 96, 98, or 99%. The microporous strong acid cation resin can be separated from the solution at the end of the reaction. The strong acid cation resin can gradually exchange at least some of the protons with ionic liquid cation. The exchanged strong acid cation resin can be regenerated by contacting with a hydrochloric acid solution, thus releasing ionic liquid cations to the solution. This spent acid solution comprising the released ionic liquid cations can be recycled back to conditioning and hydrolysis 100. This recycling can prevent loss of ionic liquid and reduce acid input in the overall process.

The resulting stream 351 can comprise from 3 to 10% glucose, not greater than 0.2% fructose, from 15 to 45% water, and from 1 to 3% hydroxymethyl furfural, and can be characterized as acidic having a pH of not greater than 1. The pH of stream 351 can be adjusted to from 2 to 3 by pH adjusting 340 with the weak acid cation resin previously loaded at least partially with ionic liquid cations, thus regenerating the weak acid cation resin to its proton form. This swing-like use of the weak acid cation resin to lower pH of the solution before dehydration and increase pH of the solution after dehydration can allow cutting the overall acid input of the process by at least 30, 40, 50, or 60%. The weak acid cation resin can be regenerated periodically with acid to allow continuous performance. The regeneration solution comprising acid and ionic liquid cations can be recycled to conditioning and hydrolysis 100.

III. Separation and Refining of Glucose

It can be desired to harvest some of the hydrolysed cellulose pulp as a refined glucose product to be used for purposes other than conversion to hydroxymethyl furfural. Glucose has numerous applications in processes as feed for fermentation and for chemical conversion processes, as well as for food and feed.

Figure 5:
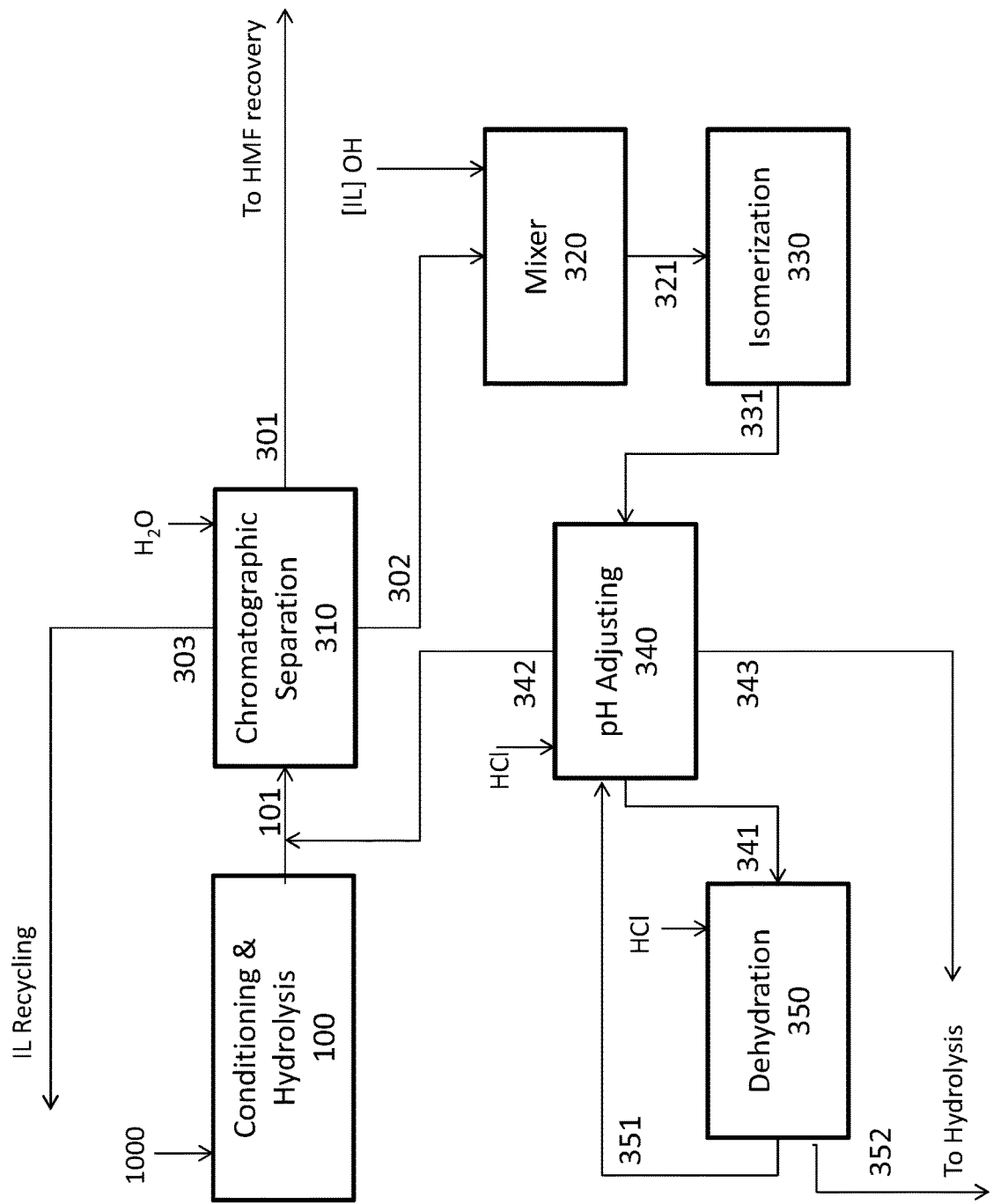
FIG. 5 illustrates a schematic diagram of an exemplary conversion process by chromatography separation, isomerization, and dehydration stages.

A process that produces glucose as an additional product stream to the overall conversion of cellulose pulp to hydroxymethyl furfural is presented in FIG. 6, which is an alternative process to the one that is provided in FIG. 5. Both processes can run side by side by diverting a portion of stream 302 to stream 311. Stream 311 can comprise from 1 to 8% glucose, and from 15 to 40% ionic liquid can feed into a second chromatography separation so as to yield stream 316 and stream 317. Stream 316 can be predominantly glucose in water, having ionic liquid concentration not greater than 5, 4, 3, 2, 1, or 0.5%. Stream 317 can be diverted back to the conversion process 300. Each chromatography separation can be optimized per overall concentration of the feed and specific concentration of compounds to be separated. The resin used for the second chromatography separation can be the same used in the first chromatography separation. Alternatively, a different resin can be used. Additionally, flow parameters can be altered or optimized for each chromatography separation to increase the overall yield or purity of the glucose product as is known in the art.

Stream 316 can be transferred to glucose refining. Refining can be achieved by contacting this stream at least one once with a strong acid cation resin, a WBA resin, a mixed bed resin, or activated carbon, or by evaporation. The stream can be first contacted with a strong acid cation resin to capture residual ionic liquid cations, these residual amounts can be recycled into the process; stream 316 can be contacted with an anion exchanger to neutralize acidity and remove residual organic acids. The anion exchanger can be selected from a WBA resin or a liquid anion exchanger, e.g., an amine extraction organic phase. The selection of the ion exchanger can be based on the efficiency and economics of this process step, e.g., if the amount of organic acid in the solution is greater than 0.1% weight to sugar weight, liquid anion exchanger can be preferred. Activated carbon can be used to remove organic impurities. A strong acid cation can be used to remove residual cations. A second WBA can be used to neutralize. Evaporation can be used to yield 30-50% dissolved solids. A mixed bed resin can be used to polish. A final evaporation can be used to yield 70% glucose solution in water.

Provided herein are compositions, including but not limited to, a glucose product composition as provided, for example, in FIG. 5 and FIG. 6.

Compositions provided herein can comprise i) at least 95% C6 carbohydrates (weight/dry solids); ii) at least 90% monosaccharides (weight/dry solids); iii) at least 90% glucose (weight/dry solids); iv) at least one non-glucose C6 carbohydrate, wherein at least 90% of the non-glucose C6 carbohydrate is mannose (weight/weight); and v) at least 100 ppb of a marker molecule, wherein the marker molecule is selected from an ionic liquid cation, imidazole, an imidazole derivative, an imidazole-sugar adjuvant, hydroxymethyl furfural, or solvent S3.

In some instances, the compositions can comprise not greater than 99% C6 carbohydrates (weight/dry solids). In some instances, the compositions can comprise from 95 to 99%, or 90, 91, 92, 93, 94, 95, 96, 97, 98, or 99% C6 carbohydrates (weight/dry solids). In some instances, the compositions can comprise not greater than 99% monosaccharides (weight/dry solids). In some instances, the compositions can comprise from 90 to 99%, or 90, 91, 92, 93, 94, 95, 96, 97, 98, or 99% monosaccharides (weight/dry solids). In some instances, the compositions can comprise not greater than 99% glucose (weight/dry solids). In some instances, the compositions can comprise from 90 to 99%, or 90, 91, 92, 93, 94, 95, 96, 97, 98, or 99% glucose (weight/dry solids). In some instances, the compositions can comprise not greater than 99% mannose to the non-glucose C6 carbohydrate (weight/weight). In some instances, the compositions can comprise from 90 to 99%, or 90, 91, 92, 93, 94, 95, 96, 97, 98, or 99% mannose to the non-glucose C6 carbohydrate (weight/weight). In some instances, the compositions can comprise 5000 ppm (5,000,000 ppb) of the marker molecule, wherein the marker molecule is selected from an ionic liquid cation, imidazole, an imidazole derivative, an imidazole-sugar adjuvant, hydroxymethyl furfural, or solvent S3. In some instances, the compositions can comprise from 100 ppb to 5000 ppm (5,000,000 ppb) of the marker molecule, wherein the marker molecule is selected from an ionic liquid cation, imidazole, an imidazole derivative, an imidazole-sugar adjuvant, hydroxymethyl furfural, or solvent S3.

In some instances, the compositions can comprise 70% glucose solution in water. In some instances, the compositions can comprise at least 90, 91, 92, 93, 94, 95, 96, or 97% C6 sugars. At least 60, 70, 80, or 90% weight/total sugar weight of the sugars can be glucose, and at least 90, 95, or 98% of the remainder sugar can be mannose. At least 90, 91, 92, 93, 94, 95, 96, 97, or 98% of the sugar can be in monomeric form. In some instances, the compositions can comprise at least 100 ppb of a marker molecule, wherein the marker molecule is selected from the ionic liquid cation, imidazole, an imidazole derivative, an imidazole-sugar adjuvant, hydroxymethyl furfural, or solvent S3.

IV. Recovery of Hydroxymethyl Furfural

Figure 7:
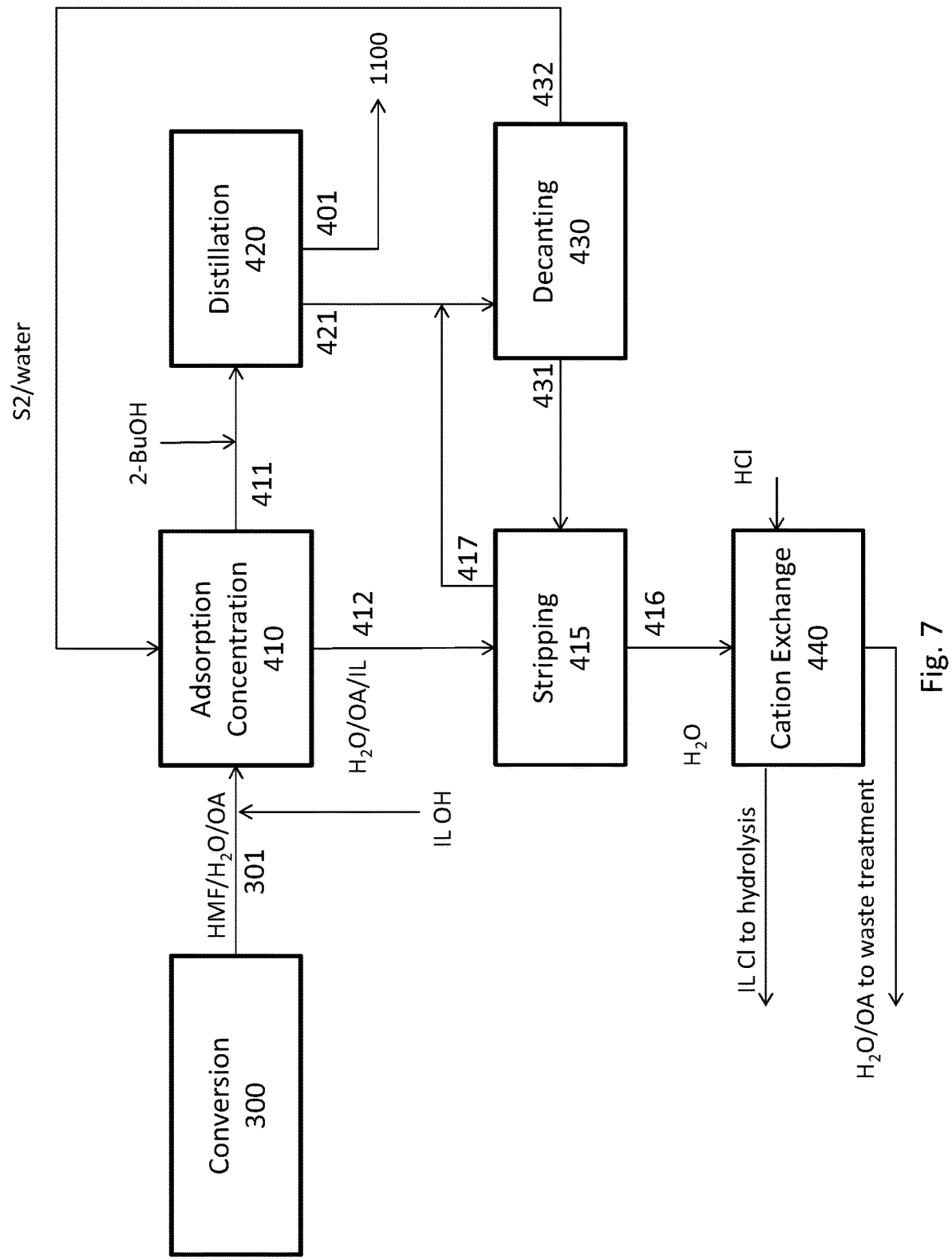
FIG. 7 illustrates a schematic diagram of an exemplary process for the recovery of hydroxymethyl furfural as a solution in a solvent, e.g., 2-butanol, from the aqueous solution; organic acids present in the aqueous phase remain in the aqueous phase.

Stream 301 in FIG. 3, FIG. 5, and FIG. 6 can be the product stream, wherein the product stream can comprise hydroxymethyl furfural. The concentration of hydroxymethyl furfural in the product stream can be low, typically not greater than 5, 4, 3, 2, or 1% (weight/weight). Stream 301 can comprise residual amounts of organic acids formed by degradation of hydroxymethyl furfural or furfural, e.g., formic acid and levulinic acid. It can be desirable to implement a cost effective method to recover hydroxymethyl furfural and refine it from this highly diluted solution. FIG. 7 presents a system and a process for efficient and energy effective recovery of hydroxymethyl furfural from the dilute stream. A non-functional polymeric (NF) resin reported to have high affinity to hydroxymethyl furfural can be used in adsorption concentration 410 to adsorb hydroxymethyl furfural product from the dilute aqueous solution, thus acting as a trap. A suitable non-functional polymeric resin can be Purolite Hypersol-Macronet® MN200, or any other similar non-functional polymeric resin used in the art. This non-functional polymeric resin does not capture organic acids when deprotonated, thus hydroxymethyl furfural is captured while eluting the organic acid with the rinse by controlling the pH above the deprotonation pH of these acids. The pH of the solution can be adjusted to from 6.5 to 7.5 by mixing ionic liquid in the hydroxide form before contacting with the non-functional polymeric resin. Once the resin gets near full or to full capacity, the trapped hydroxymethyl furfural can be desorbed from the resin with a much reduced volume of solvent S2:water solution, at a ratio of from 80:20 to 99:1.

Solvent S2 can be characterized by having the ability to solubilize hydroxymethyl furfural. Solvent S2 can be characterized by the formation of a heterogeneous azeotrope with water, wherein the azeotrope boiling point is up to 90° C. and is lower than the boiling point of solvent S2. Preferably, water solubility in the solvent is low and solvent solubility in the aqueous phase is low. Solvent S2 can be selected from ethyl acetate, methanol, ethanol, isopropanol, 1-butanol, 2-butanol, or a combination thereof. Solvent S2 can be ethyl acetate.

The non-functional polymeric resin can be used to recover hydroxymethyl furfural and remove organic acids, where ethyl acetate can act as a regeneration media. The adsorption-desorption action of 410 can reduce the energy cost for recovering hydroxymethyl furfural by a factor of at least 5, 7, 10, 15, or 20, because the solvent weight of stream 411 can be a 2, 4, 6, 8, 10, 20, 50, or 100 fold reduction compared to stream 301, and also because the relative part of water to ethyl acetate can be reduced from 100% weight/weight to from 3 to 4% weight/weight. Stream 411 can be transferred to a distillation 420, where ethyl acetate can be boiled off at 70.4, or 70, 70.4, 70.5, or 71° C. The vapor stream 421 can be transferred to decanting 430, to separate water from solvent. The resulting stream 432 can comprise 97:3 ethyl acetate:water and can be then recycled for further use. The aqueous phase 431 can be transferred to a stripper 415 to remove by evaporation residual amounts of the solvent through stream 417. Stream 416 can be contacted with a weak acid cation resin in the proton form to capture residual ionic liquid cations in cation exchange 440, which can be regenerated by contacting the weak acid cation resin with acid and recycling the ionic liquid cations to hydrolysis. The aqueous stream that is stripped of ionic liquid cations can be transferred to a waste water treatment plant where the organic acids can be fermented to produce methane. Before, during, or after distillation, a solvent of higher boiling point can be added as a suitable co-solvent for hydroxymethyl furfural, as needed for the next stage of use of hydroxymethyl furfural. A solvent of higher boiling point can be selected from 2-butanol, 2-propanol, tetralin, or water, or a combination thereof. A solvent of higher boiling point can be 2-butanol. Product 1100 can comprise at least 5, 10, 15, 20, 25, or 30% hydroxymethyl furfural. Product 1100 can comprise at least 50 ppb of a marker molecule, wherein the marker molecule is selected from ethyl acetate, water, ionic liquid cation, furfural, levulinate anion, formate anion, glucose, fructose, mannose, or adducts of sugar and the ionic liquid cation. Product 1100 can also comprise at least 50 ppb of a marker molecule, wherein the marker molecule is selected from ethyl acetate, ionic liquid cation, furfural, levulinate anion, formate anion, glucose, fructose, or mannose.

Provided herein are compositions, including but not limited to, product 1100 as provided, for example, in FIG. 7.

Compositions provided herein can comprise at least 5% hydroxymethyl furfural (weight/weight) and not greater than 95% of a solvent (weight/weight), wherein the solvent is selected from 2-butanol, 2-propanol, tetralin, or water, or a combination thereof. In some instances, the compositions can comprise at least 50 ppb of a marker molecule, wherein the marker molecule is selected from ethyl acetate, ionic liquid cation, furfural, levulinate anion, formate anion, levulinic acid, formic acid, glucose, fructose, or mannose. In some instances, the compositions can comprise not greater than 50% hydroxymethyl furfural (weight/weight). In some instances, the compositions can comprise from 5 to 50%, or 5, 10, 15, 20, 25, 30, 35, 40, 45, or 50% hydroxymethyl furfural (weight/weight). In some instances, the compositions can comprise not greater than 10% hydroxymethyl furfural (weight/weight). In some instances, the compositions can comprise from 5 to 10% hydroxymethyl furfural (weight/weight). In some instances, the compositions can comprise 5000 ppm (5,000,000 ppb) of the marker molecule, wherein the marker molecule is selected from ethyl acetate, ionic liquid cation, furfural, levulinate anion, formate anion, levulinic acid, formic acid, glucose, fructose, or mannose. In some instances, the compositions can comprise from 50 ppb to 5000 ppm (5,000,000 ppb) of the marker molecule, wherein the marker molecule is selected from ethyl acetate, ionic liquid cation, furfural, levulinate anion, formate anion, levulinic acid, formic acid, glucose, fructose, or mannose.

V. Recycling of Ionic Liquid

Ionic liquids have advantages as reaction media over traditional solvents because they are typically not volatile or flammable, and because some ionic liquids are environmentally safe due to their low ecotoxicity. Certain ionic liquids can be highly effective in dissolving crystalline cellulose. A potential disadvantage of ionic liquid can be high cost. It can be beneficial to design very effective recycling of the ionic liquid in the processes disclosed herein in order to avoid waste of the ionic liquid, and associated increased costs. Methods and processes of trapping and/or recycling the ionic liquid are provided herein.

a) Trapping of Ionic Liquid Cations in Dilute Aqueous Streams

Trapping and/or recycling ionic liquid can comprise treating each dilute aqueous stream (e.g., dilute aqueous streams directed to waste treatment) with a weak acid cation resin in order to cause the adsorption of the ionic liquid cation, e.g., the 1-ethyl-3-methylimidazolium cation or 1-butyl-3-methylimidazolium cation form. The ionic liquid cation can be regenerated by contacting the resin with an acid stream, or such stream can be a strong acid cation resin effluent stream having excess of protons to reduce overall usage of water and acid in the process.

b) Recycling of Ionic Liquid for Cellulose Solubilizing

The processes disclosed herein can comprise using water, and it can be desirable to remove water from the ionic liquid during recycling for cellulose solubilization because water precipitates cellulose before cellulose is hydrolyzed. Water removal can be achieved by adding a solvent S3 that mixes with ionic liquid and water, and forms a heterogeneous azeotrope with water, where the azeotrope boiling point can be not greater than 100° C. at 100 mm Hg and where the solvent miscibility with water can be not greater than 1%. The solvent S3 can be a linear or branched C8, C9, C10, C11, or C12 alkyl substituted with at least one substituent selected from hydroxy, oxo, nitrile, or halide. The solvent S3 can be a linear or branched C5, C6, or C7 aryl substituted with at least one substituent selected from hydroxy, oxo, nitrile, or halide. The solvent S3 can be selected from cyclohexanol, 2-ethyl-1-hexanol, hexyl chloride, butyronitrile, cyclohexanone, cyclopentanone, diisobutyl ketone, dipropyl ketone, mesityl oxide, methylamyl ketone, 2,4-pentandione, 2,3-dichloropropanol, dichloropentadiene, ethylbenzene, styrene, or xylene. The azeotrope distillation can be performed under reduced pressure at not greater than 100, 80, or 60° C. The energy requirement to evaporate 1 kg of water can be reduced to not greater than 80, 70, 60, 50, or 40% of the energy required for direct evaporation of water from the ionic liquid phase.

Figure 8:
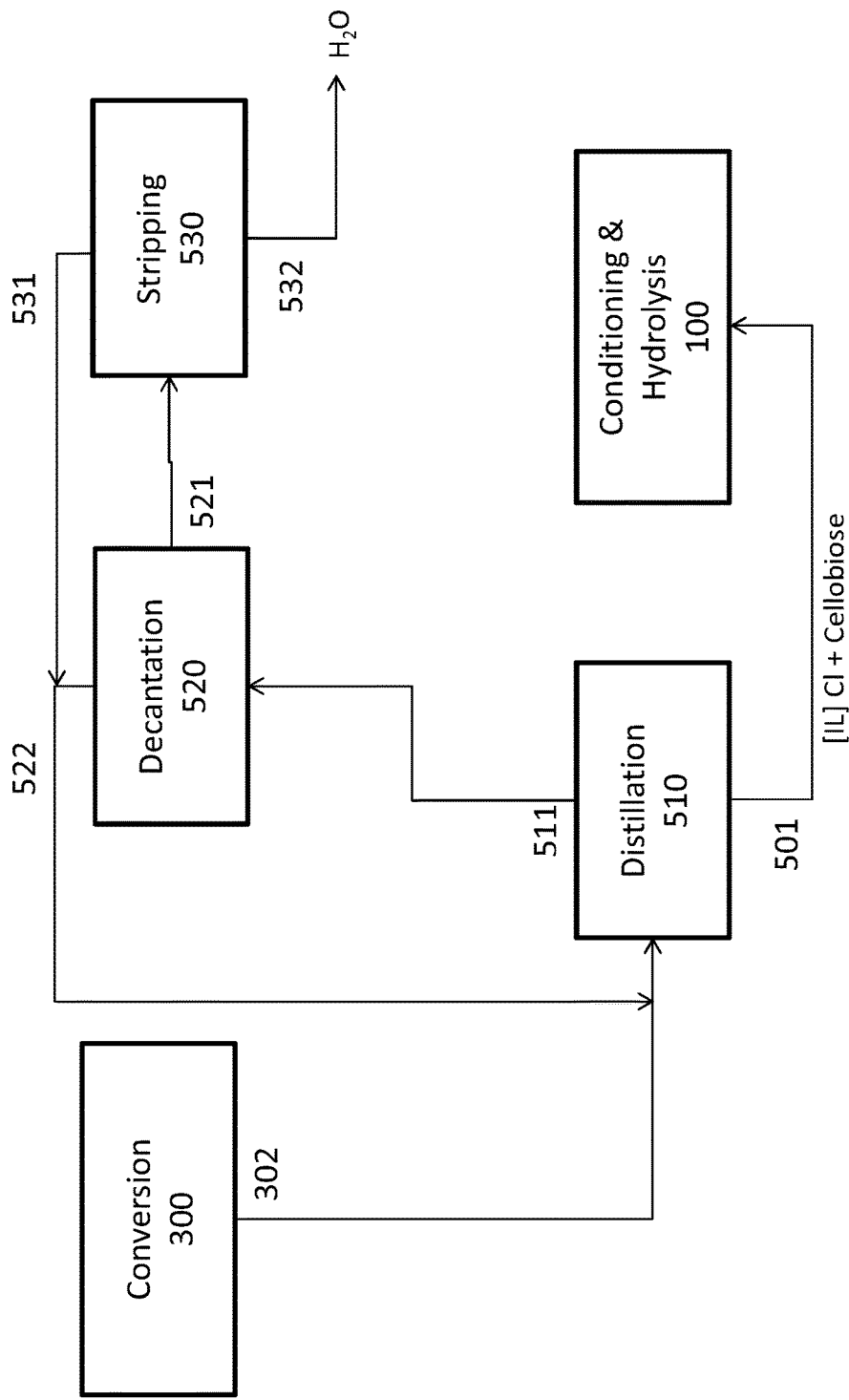
FIG. 8 illustrates a schematic diagram of an exemplary process for drying of the ionic liquid and recycling it for further use.

Provided herein are compositions, including but not limited to, stream 501 as provided, for example, in FIG. 8.

Compositions provided herein can comprise i) at least 95% ionic liquid (weight/weight); ii) from 0.1 to 2% cellobiose (weight/weight); iii) not greater than 0.1% fructose (weight/weight); iv) not greater than 0.1% hydroxymethyl furfural (weight/weight); v) not greater than 4% water (weight/weight); and vi) not greater than 2% solvent S3 (weight/weight). In some instances, the compositions can comprise i) at least 95% ionic liquid (weight/weight); ii) from 0.1 to 2% cellobiose (weight/weight); iii) not greater than 0.1% fructose (weight/weight); iv) not greater than 0.1% hydroxymethyl furfural (weight/weight); v) not greater than 4% water (weight/weight); vi) not greater than 2% solvent S3 (weight/weight); and at least one of the following characteristics: i) from 0.1 to 3% glucose (weight/weight); ii) not greater than 0.1% mannose (weight/weight); iv) not greater than 0.1% levulinic acid (weight/weight); and v) not greater than 0.1% formic acid (weight/weight).

In some instances, the compositions can comprise i) at least 95% ionic liquid (weight/weight); ii) from 0.1 to 2% cellobiose (weight/weight); iii) not greater than 0.1% fructose (weight/weight); iv) not greater than 0.1% hydroxymethyl furfural (weight/weight); v) not greater than 4% water (weight/weight); vi) not greater than 2% solvent S3 (weight/weight); and at least two of the following characteristics: i) from 0.1 to 3% glucose (weight/weight); ii) not greater than 0.1% mannose (weight/weight); iv) not greater than 0.1% levulinic acid (weight/weight); and v) not greater than 0.1% formic acid (weight/weight).

In some instances, the compositions can comprise i) at least 95% ionic liquid (weight/weight); ii) from 0.1 to 2% cellobiose (weight/weight); iii) not greater than 0.1% fructose (weight/weight); iv) not greater than 0.1% hydroxymethyl furfural (weight/weight); v) not greater than 4% water (weight/weight); vi) not greater than 2% solvent S3 (weight/weight); and at least three of the following characteristics: i) from 0.1 to 3% glucose (weight/weight); ii) not greater than 0.1% mannose (weight/weight); iv) not greater than 0.1% levulinic acid (weight/weight); and v) not greater than 0.1% formic acid (weight/weight).

In some instances, the compositions provided herein can comprise at least 94, 95, 96, 97, 98, or 99% ionic liquid (weight/weight). In some instances, the compositions provided herein can comprise not greater than 99.7% ionic liquid (weight/weight). In some instances, the compositions provided herein can comprise from 95 to 99.7% ionic liquid (weight/weight). In some instances, the compositions provided herein can comprise at least 0.001% fructose (weight/weight). In some instances, the compositions provided herein can comprise from 0.001 to 0.1%, or 0.001, 0.005, 0.01, 0.05, or 0.1% fructose (weight/weight). In some instances, the compositions provided herein can comprise at least 0.001% hydroxymethyl furfural (weight/weight). In some instances, the compositions provided herein can comprise from 0.001 to 0.1%, or 0.001, 0.005, 0.01, 0.05, or 0.1% hydroxymethyl furfural (weight/weight). In some instances, the compositions provided herein can comprise at least 0.4% water (weight/weight). In some instances, the compositions provided herein can comprise from 0.4 to 4%, or 0.4, 0.5, 1, 1.5, 2, 2.5, 3, 3.5, or 4% water (weight/weight). In some instances, the compositions provided herein can comprise at least 0.2% solvent S3 (weight/weight). In some instances, the compositions provided herein can comprise from 0.2 to 2%, or 0.2, 0.5, 1, 1.5, or 2% solvent S3 (weight/weight). In some instances, the compositions provided herein can comprise at least 0.001% mannose (weight/weight). In some instances, the compositions provided herein can comprise from 0.001 to 0.1%, or 0.001, 0.005, 0.01, 0.05, or 0.1% mannose (weight/weight). In some instances, the compositions provided herein can comprise at least 0.001% levulinic acid (weight/weight). In some instances, the compositions provided herein can comprise from 0.001 to 0.1%, or 0.001, 0.005, 0.01, 0.05, or 0.1% levulinic acid (weight/weight). In some instances, the compositions provided herein can comprise 0.001% formic acid (weight/weight). In some instances, the compositions provided herein can comprise from 0.001 to 0.1%, or 0.001, 0.005, 0.01, 0.05, or 0.1% formic acid (weight/weight).

In some instances, the compositions provided herein can comprise at least one compound selected from cellobiose, glucose, fructose, mannose, hydroxymethyl furfural, levulinic acid, formic acid, water, or solvent S3. In some instances, the compositions provided herein can comprise from 0.1 to 2% cellobiose (weight/weight); from 0.1 to 3% glucose (weight/weight); not greater than 0.1, 0.05, or 0.01% fructose (weight/weight); not greater than 0.1, 0.05, or 0.01% mannose (weight/weight); not greater than 0.1, 0.05, or 0.01% hydroxymethyl furfural (weight/weight); not greater than 0.1, 0.05, 0.01, 0.005, or 0.001% levulinic acid (weight/weight); not greater than 0.1, 0.05, 0.01, 0.005, or 0.001% formic acid (weight/weight); 0.1, 0.5, 1, 1.5, 2, 2.5, 3, 3.5, or 4% water (weight/weight); and not greater than 2, 1, 0.5, 0.1, or 0.05% solvent S3 (weight/weight).

In some instances, the solvent S3 is cyclohexanol.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1—Composition of Cellulose Remainder Pulp Derived from Pine and *Eucalyptus*

Fresh wood chips were fed into a high pressure reactor and were heated to from 135 to 145° C. for from 1 to 3 hours, in a solution comprising from 0.3 to 0.5% $H_2SO_4$ and 0.2% $SO_2$. The remaining solid was separated from the liquid comprising hemicellulose sugars, ash, organic acids, acid soluble lignin, and extractives. The solid was washed with fresh acid solution and dried.

The remaining lignocellulose matter was then heated to from 160 to 210° C. for from 1 to 3 hours in a solution comprising 1:1 methyl ethyl ketone:water and from 0.5 to 1.5% (weight/weight) acetic acid. The remaining pulp was collected, washed with water-saturated methyl ethyl ketone, and dried. The composition of resulting cellulose pulp obtained was characterized according to NREL method TP-510-42618. Ash was determined according to NREL method TP-510-42622.

TABLE 1A

Composition of cellulose remainder pulp

| Sample (ref) | $C_6$ sugars (glucose) % wt/wt (% wt/wt) | $C_5$ sugars % wt/wt | Total sugars % wt/wt | Lignin % wt/wt | Ash % wt/wt |
|---|---|---|---|---|---|
| Eucalyptus (60 min@ 160° C., 0.5% acid) (18789) | 57.0 (53.2) | 3.8 | 60.8 | 18.23 | 0.11 |
| Eucalyptus (180 min@ 160° C., 0.5% acid) (18790) | 70.7 (66.8) | 3.8 | 73.8 | 11.35 | 0.1 |
| Pine (60 min@ 170° C., 0.5% acid) (18791) | 52.6 (47.3) | 4.1 | 56.7 | 37.43 | 0.39 |
| Pine (120 min@ 200° C., 1.5% acid) | 63.4 (60.5) | 1.5 | 64.9 | 23.8 | 0.52 |

TABLE 1B

Remaining cellulose pulps obtained through this process were analyzed by ICP

| Sample reference | Species | S | Ca | Fe | K | Mg | Na |
|---|---|---|---|---|---|---|---|
| 16995 | Eucalyptus | 400 | 150 | 160 | 40 | 20 | 30 |
| 16998 | Eucalyptus | 430 | 110 | 100 | 30 | 6 | 10 |
| 18104 | Pine | 530 | 40 | 130 | 150 | 80 | 10 |
| 18116 | Pine | 400 | 40 | 200 | 70 | 20 | 2 |

TABLE 2

Composition of the cellulose remainder pulp

| Time (h) | Temperature (° C.) | % AcOH | Remainder Solid (g/100 g initial solid) | % Lignin | % Cellulose |
|---|---|---|---|---|---|
| 2 | 175 | 2.5 | 54.7 | 2.1 | 96.2 |
| 1 | 190 | 0.5 | 54.2 | 10.6 | 80.4 |
| 3 | 160 | 0.5 | 60.5 | 7.5 | 87.6 |

Example 2—Composition of Cellulose Remainder Pulp Derived from Eucalyptus

Eucalyptus feedstock was treated to extract hemicellulose sugars, ash, and acid soluble lignin as described in Example 1. The lignocellulosic remainder was milled to produce powder of about 1400 micron. The milled powder, approximately 20 g and 5% moisture, was loaded in a pressure reactor. 100 g of water and 80 g methylethyl ketone were added to the reactor, and acetic acid 0.5% to 2.5% wt/wt to total liquids. The reactor was heated to 160-190° C. for 1-3 hours. The reactor was cooled down, and solid and liquid separated. The solid was washed with additional amount of water saturated MEK solution, and dried under vacuum.

The amount of cellulose and lignin in the remainder solid was measured according to NREL/TP-510-42618. The results indicate high efficiency of the reaction conditions in extracting lignin, leaving behind down to less than 5% lignin (weight/weight) solid under optimal conditions, with as low as 2% achievable.

Example 3—Composition of Cellulose Remainder Pulp Derived from Eucalyptus

The procedure of Example 2 was scaled up by fifteenfold to a seven liter pressure reactor. Hemi-depleted eucalyptus was ground, various reaction conditions were tested, and the composition of the resulting pulp was characterized. The results are summarized in Table 3.

TABLE 3

Composition of the cellulose remainder pulp

| Lot# | $H_2O$/solid | Acetic Acid, (%) | MEK/$H_2O$ | Time (min) | Temp (° C.) | Ash (%) | K Lignin (%) | ASL (%) | Cellulose (%) | Hemi (%) |
|---|---|---|---|---|---|---|---|---|---|---|
| Hemi Depleted Eucalypt. |  |  |  |  |  | 0.2 | 34.2 | 4.3 | 46.7 | 8.2 |
| DB-121113-1 | 10 | 0.5 | 50:50 | 180 | 180 | 0.2 | 3.5 | 2.1 | 85.7 | 4.2 |
| DB-031214-1 | 10 | 1.0 | 50:50 | 120 | 187 | 0.2 | 5.2 | 2.1 | 79.6 | 4.1 |
| DD-031414-1 | 10 | 1.0 | 50:50 | 120 | 190-192 | 0.2 | 5.2 | 2.0 | 76.6 | 3.6 |
| DB-031814-1 | 10 | 1.0 | 50:50 | 150 | 192 | 0.2 | 5.7 | 2.1 | 79.1 | 3.3 |

Example 4—Composition of Cellulose Remainder Pulp Derived from Bagasse

Bagasse was de-ashed by applying several cycles of shear treatment and washing with high pressure to cause the removal of stones, sand, and ash. The resulting de-ashed biomass was treated by heating with 0.5% $H_2SO_4$ (16:1 weight/weight) at from 135 to 145° C. for from 0.5 to 3 hours to extract the hemicellulose, ASL, organic acid, and remaining ash. The remaining lignocellulose matter was then heated to from 160 to 210° C. for from 1 to 3 hours in a solution comprising 1:1 methyl ethyl ketone:water and from 0.5 to 1.5% (weight/weight) acetic acid. The remaining pulp was collected, washed with water-saturated methyl ethyl ketone, and dried. The composition of resulting cellulose pulp obtained was characterized according to NREL method TP-510-42618. Ash was determined according to NREL method TP-510-42622.

TABLE 4

Composition of cellulose remainder pulp

| Composition | wt. % |
|---|---|
| Glucan | 84.40 ± 0.40 |
| Xylan | 1.95 ± 0.03 |
| Lignin | 7.49 ± 0.59 |
| Ash | 5.08 ± 0.12 |
| Others | 1.08 ± 0.72 |

Example 5—Solubility Properties of Cellulose Remainder Pulp

The pulps were characterized by their solubility in water and ether, in comparison to Avicel PH-200. The results are summarized in Table 5.

TABLE 5

Solubility properties of various cellulose pulps

| | LIMS | pH | Conductivity µS/cm | Water soluble substances % | Water soluble substances mg/5 gr | Ether soluble substances mg/10 gr |
|---|---|---|---|---|---|---|
| Avicel PH-200 | Literature* | 5.5-7 | 75 | 0.25 | 12.5 | 5 |
| Bagasse | 17558 | 5.7-6.4 | 15-30 | 0.21 | 10.7 | 19.6 |
| Pine | 18578 | 4.4-4.6 | 35-50 | 0.19 | 9.7 | 19.8 |
| Eucalyptus | 16995 | 4.2-4.5 | 45-65 | 0.25 | 12.7 | 2.2 |

*Published online: http://www.signetchem.com/downloads/datasheets/Fmc-biopolymer/Avicel-Ph-200-Specifications.pdf

Example 6—Composition of Cellulose Remainder Pulp Derived from Bagasse and Eucalyptus Bagasse and eucalyptus feedstocks were treated as in Example 1 in order to first extract hemicellulose, and then extract lignin. The cellulose remainder pulp was characterized. The results are summarized in Table 6.

TABLE 6

Characterization of bagasse and eucalyptus cellulose pulps

| Chemical property (method) | Bagasse | Eucalyptus |
|---|---|---|
| Lignin, wt % (T249: NREL/TP-510-42618) | 10.14 | 5.84 |
| Acid Insoluble, wt % | 9.67 | 5.43 |
| Acid Soluble, wt % | 0.47 | 0.41 |
| Sugars (T249: NREL/TP-510-42618) | 90.59 | 92.90 |
| Arabinan, wt % | <0.01 | <0.01 |
| Galactan, wt % | <0.01 | <0.01 |
| Glucan, wt % | 87.88 | 92.39 |
| Xylan wt % | 2.63 | 0.51 |
| Mannan, wt % | <0.01 | <0.01 |
| Alpha Cellulose, wt % (T203) | 63.6 | 35.0 |
| Beta Cellulose, wt % (T203) | 35.2 | 63.5 |
| Gamma Cellulose, wt % (T203) | 1.2 | 1.4 |
| DCM Extractives (T204) | 0.097 | 0.097 |
| Ash Content, wt % (T211) | 1.54 | 0.196 |

Figure 9:
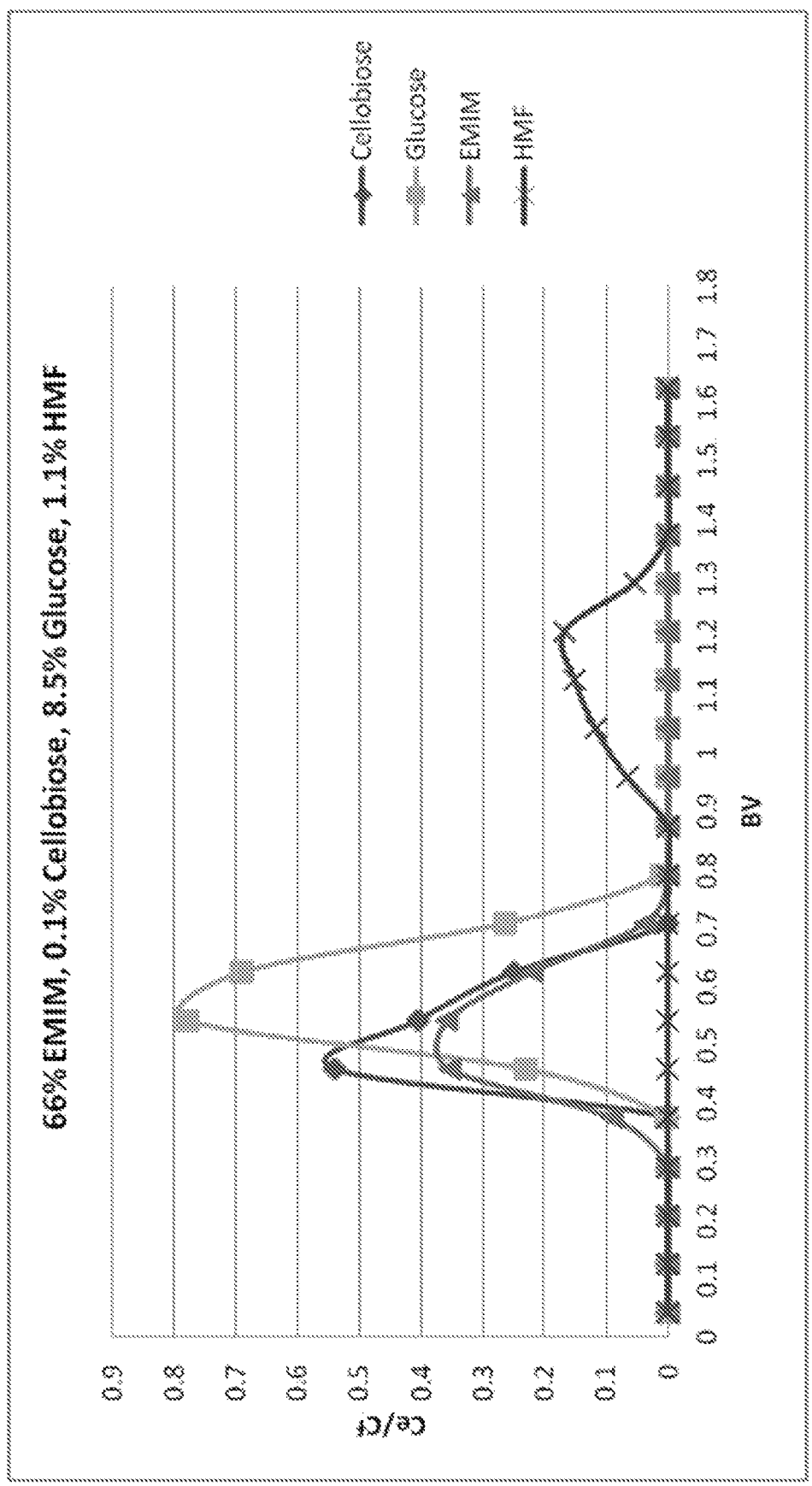
FIG. 9 illustrates results of a pulse test showing separation by chromatography of 1-ethyl-3-methylimidazolium chloride, saccharides, and hydroxymethyl furfural.

Example 7: Chromatography Separation of Hydroxymethyl Furfural/Glucose/Cellobiose/Ionic Liquid A mixture of glucose, hydroxymethyl furfural, cellobiose, and 1-ethyl-3-methylimidazolium chloride was passed through the resin PCR-642 in the 1-ethyl-3-methylimidazolium form. A 240 mL volume at diameter of 2.5 cm was used, and the run was conducted at 60° C. The column was eluted with deionized water at a rate of 8 ml/min. Fractions of 10 mL were collected, for a total of 600 mL, and analyzed by HPLC on an Aminex HPX-87H column. The resulting profiles are seen in FIG. 9.

Example 8: Isomerization of Glucose to Fructose

A 22% 1-butyl-3-methylimidazolium chloride and 3% glucose solution in water was titrated to the desired pH with a 10% 1-butyl-3-methylimidazolium hydroxide stock solution. 3.0 g of stock solution was weighed into five glass vessels outfitted with a stir bar and air tight cap. Reactions were heated with one vessel taken and cooled for each time. Each aqueous sample was diluted tenfold by a 0.1 M hydrochloric acid solution (in water) to neutralize the base, and the sample was filtered for injection on an Aminex HPX-87H column and/or Dionex CarboPac SA-10 column HPAE, with detection by pulse amperometry detector (PAD). Results are summarized in Table 6. The Aminex HPX-87H column does not resolve fructose, mannose, and xylose (a C5 impurity in the sugar). Samples with high non-glucose sugar selectivity were run on the Dionex to distinguish fructose, mannose, and xylose.

TABLE 8

Isomerization of glucose to fructose

| Temp (° C.) | Time (min) | Initial pH | Initial % wt/wt water | BMIMCl | Glucose | BMIMOH 10% | Best result % wt/wt Glucose | Fructose | Mannose | Mass Balance | Glucose Conv. | Fructose Yield | Fructose Sel. | Mannose Yield | Mannose Sel. |
|---|---|---|---|---|---|---|---|---|---|---|---|---|---|---|---|
| 45 | 240 | 11 | 71.8 | 21.2 | 3.02 | 3.98 | 2.52 | 0.45 | — | 99.40 | 15.70 | 15.09 | 96.19 | — | — |
| 50 | 60 | 11.17 | 63.3 | 18.6 | 2.53 | 15.55 | 1.84 | 0.60 | — | 98.82 | 25.50 | 24.31 | 95.38 | — | — |
| 55 | 240 | 11 | 72.7 | 21.5 | 3.06 | 2.78 | 1.62 | 0.79 | 0.02 | 101.03 | 25.80 | 24.05 | 93.33 | 2.75 | 10.67 |
| 55 | 240 | 10 | 74.3 | 22.1 | 2.97 | 0.07 | 2.88 | 0.11 | — | 100.30 | 3.50 | 3.53 | 100.82 | — | — |
| 55 | 240 | 10.5 | 73.7 | 21.9 | 2.95 | 1.49 | 2.76 | 0.20 | — | 99.75 | 7.10 | 6.88 | 96.52 | — | — |
| 60 | 40 | 10.95 | 68.7 | 20.2 | 2.75 | 8.40 | 1.81 | 0.70 | 0.11 | 95.89 | 34.14 | 25.47 | 74.62 | 4.00 | 11.73 |
| 80 | 15 | 11 | 72.0 | 21.1 | 2.88 | 3.99 | 1.83 | 0.89 | — | 97.10 | 34.60 | 31.74 | 91.64 | — | — |
| 55 | 180 | 10.94 | 41.7 | 48.0 | 6.89 | 3.46 | 5.35 | 1.23 | 0.03 | 95.98 | 22.32 | 17.89 | 80.14 | — | — |
| 55 | 180 | 11.5 | 56.1 | 25.8 | 3.71 | 14.42 | 1.84 | 1.44 | 0.04 | 92.95 | 50.49 | 38.81 | 76.86 | — | — |
| 55 | 180 | 12.00 | 44.7 | 20.5 | 2.96 | 31.79 | 1.18 | 1.31 | 0.08 | 94.81 | 60.10 | 44.17 | 73.49 | — | — |
| 45 | 180 | 11.50 | 53.3 | 30.4 | 3.99 | 12.32 | 2.29 | 1.10 | 0.14 | 93.51 | 39.20 | 29.14 | 74.24 | 3.61 | 9.21 |
| 45 | 180 | 11.90 | 46.9 | 26.8 | 3.51 | 22.76 | 1.75 | 1.15 | 0.17 | 91.85 | 47.60 | 34.44 | 72.38 | 4.99 | 10.49 |
| 45 | 180 | 11.90 | 46.6 | 28.4 | 4.06 | 20.88 | 2.36 | 1.32 | 0.19 | 98.43 | 42.00 | 32.48 | 77.34 | 4.64 | 11.05 |

Example 9: Dehydration of Fructose to Hydroxymethyl Furfural

The dehydration reaction of a solution comprising fructose, glucose, 1-butyl-3-methylimidazolium chloride, and water, using a strong acid cation resin as catalyst, was conducted. The reaction conditions and products are summarized in Table 9, the data indicating high specific conversion of fructose to hydroxymethyl furfural and that glucose is mostly unchanged. The strong acid cation resins tested were Purolite CT275DR SAC Resin or Rohm & Haas Amberlyst-15.

were passed through the column, and fractioned into 1 BV samples. The samples were filtered and analyzed by HPLC equipped with an Aminex HPX-87H column. The organic acids passed through the column without being adsorbed by the resin. The concentration for organic acids after BV 3 was consistent with the concentration in the feed. The concentration of the organic acids in the first two bed volumes were lower than the feed because it was being diluted by the rinse wash left in the column. No hydroxymethyl furfural was detected in the effluent until BV 17 and further to higher BV, indicating the capacity of the resin had been fully loaded.

TABLE 9

Dehydration of fructose to hydroxymethyl furfural

| % Water | Temperature | Residence Time | Catalyst Loading % of solution: | Glucose Conversion, mol % | Fructose Conversion, mol % | HMF Yield, mol % | HMF Selectivity, % | Molar Sugar Balance, % |
|---|---|---|---|---|---|---|---|---|
| 15% | T = 85° C. | 60 min | 9.2% SAC | 8.88 | 99.16 | 28.69 | 78.35 | 92.07 |
| 15% | T = 75° C. | 45 min | 9.5% SAC | 0.79 | 97.99 | 27.94 | 89.61 | 96.76 |
| 15% | T = 70° C. | 45 min | 10.5% SAC | 0.87 | 92.04 | 27.84 | 95.70 | 98.75 |
| 30% | T = 85° C. | 60 min | 7.8% SAC | 0.63 | 60.40 | 16.67 | 90.02 | 98.15 |
| 30% | T = 85° C. | 120 min | 10% SAC | 6.61 | 100.00 | 12.98 | 37.82 | 78.65 |
| 30% | T = 80° C. | 60 min | 10% SAC | 0.00 | 63.12 | 17.85 | 97.24 | 99.49 |
| 30% | T = 80° C. | 90 min | 10% SAC | 0.46 | 87.49 | 25.02 | 91.49 | 97.67 |
| 30% | T = 80° C. | 90 min | 18% SAC | 0.94 | 93.88 | 24.69 | 90.02 | 97.26 |
| 30% | T = 80° C. | 90 min | 10% SAC | 0.00 | 65.42 | 19.59 | 100.82 | 100.16 |
| 30% | T = 80° C. | 90 min | 10% Amberlyst-15 | 0.00 | 74.48 | 11.94 | 59.35 | 91.82 |
| 30% | T = 80° C. | 90 min | 10% SAC | 0.00 | 62.47 | 18.16 | 97.47 | 99.53 |
| 45% | T = 85° C. | 60 min | 5.9% SAC | 0.44 | 12.07 | 4.34 | 99.73 | 99.99 |

Example 10: Recovery and Refining of Hydroxymethyl Furfural

Approximately 30 mL of Purolite Hypersol-Macronet® MN200, 535±85 µm, nonfunctional resin was washed with deionized water in a beaker for 30 minutes. 15 mL of the washed resin was packed into the 25 mL column. The resin was flushed with 2 bed volumes (BV) of water, at 0.8 mL/min. A feed solution was made up according to Table 10, and the feed solution was adjusted to pH 7. The feed was loaded onto the column at 0.8 mL/min. A total of 20 BV

TABLE 10

| Feed composition | | | |
|---|---|---|---|
| | Mass (g) | % w/w | pKa |
| Hydroxymethyl furfural | 1.2065 | 0.302 | 12.8 |
| Water | 398.5304 | 99.633 | |
| Levulinic Acid | 0.1285 | 0.032 | 4.8 |
| Formic Acid | 0.1346 | 0.034 | 3.8 |
| Total | 400 | | |

Figure 10:
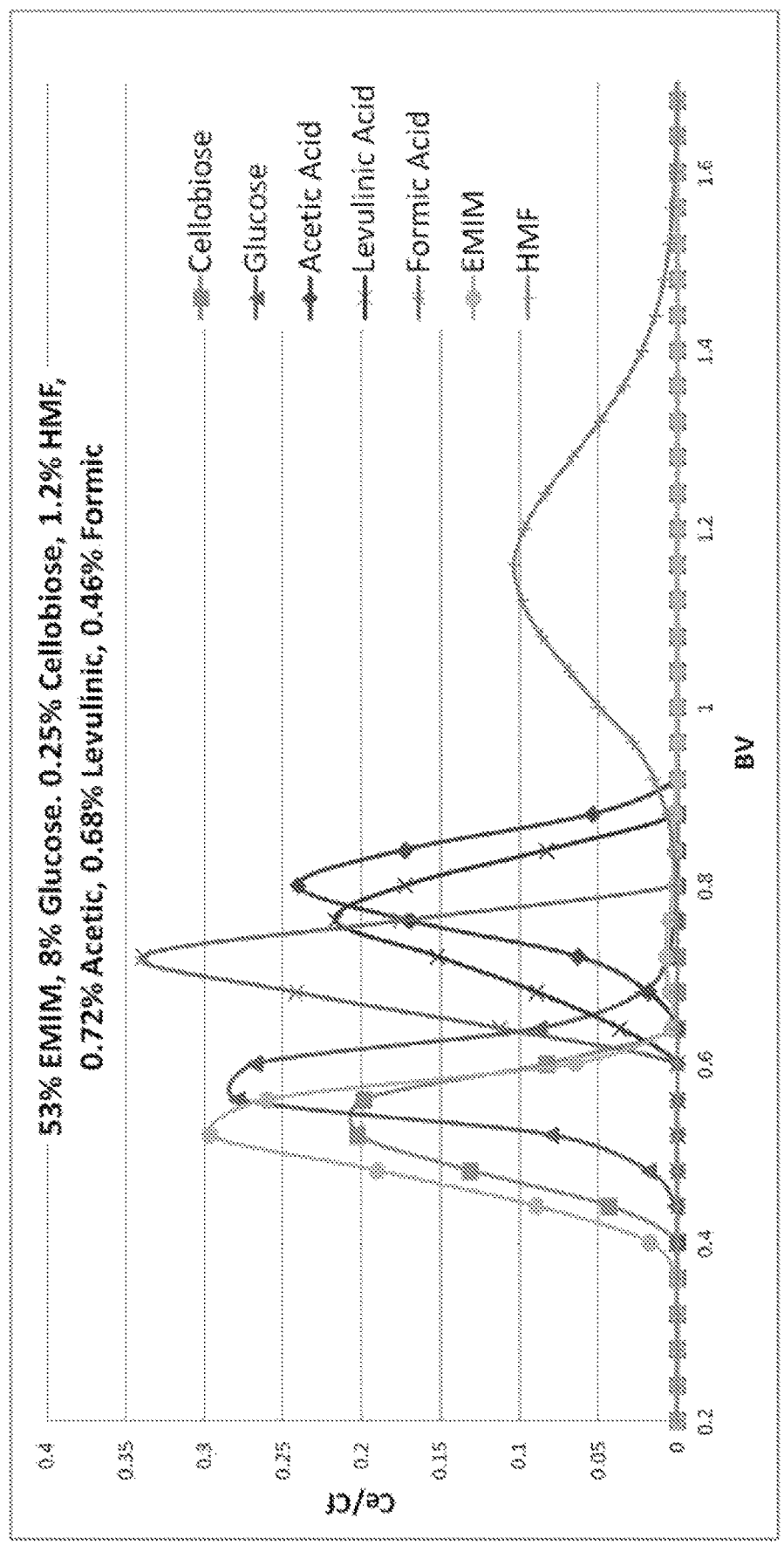
FIG. 10 illustrates results of a pulse test showing the elution of 1-butyl-3-methylimidazolium chloride, saccharides, hydroxymethyl furfural, and organic acids.

Example 11: Chromatography Separation of Hydroxymethyl Furfural/Glucose/Cellobiose/Ionic Liquid/Organic Acids An 8 ml mixture of glucose, hydroxymethyl furfural, cellobiose, and 1-ethyl-3-methylimidazolium chloride having the composition as provided in Table 11 was passed through the resin PUROLITE PCR 642 H in the 1-ethyl-3-methylimidazolium form. A 250 mL volume at diameter of 2.5 cm was used, the run conducted at 60° C. The column was eluted with deionized water at a rate of 8 ml/min. Fractions of 10 mL were collected for a total of 600 mL and analyzed by HPLC on Aminex HPX-87H column. The resulting profiles are seen in FIG. 10.

TABLE 11

Feed composition Mass Balance

|  | In (g) | Out (g) |
| --- | --- | --- |
| Ionic liquid | 4.2 | 4.8 |
| Glucose | 0.61 | 0.61 |
| Cellobiose | 0.017 | 0.016 |
| Hydroxymethyl furfural | 0.095 | 0.10 |
| Acetic Acid | 0.057 | 0.052 |
| Levulinic Acid | 0.053 | 0.051 |
| Formic Acid | 0.036 | 0.039 |

Figure 11:
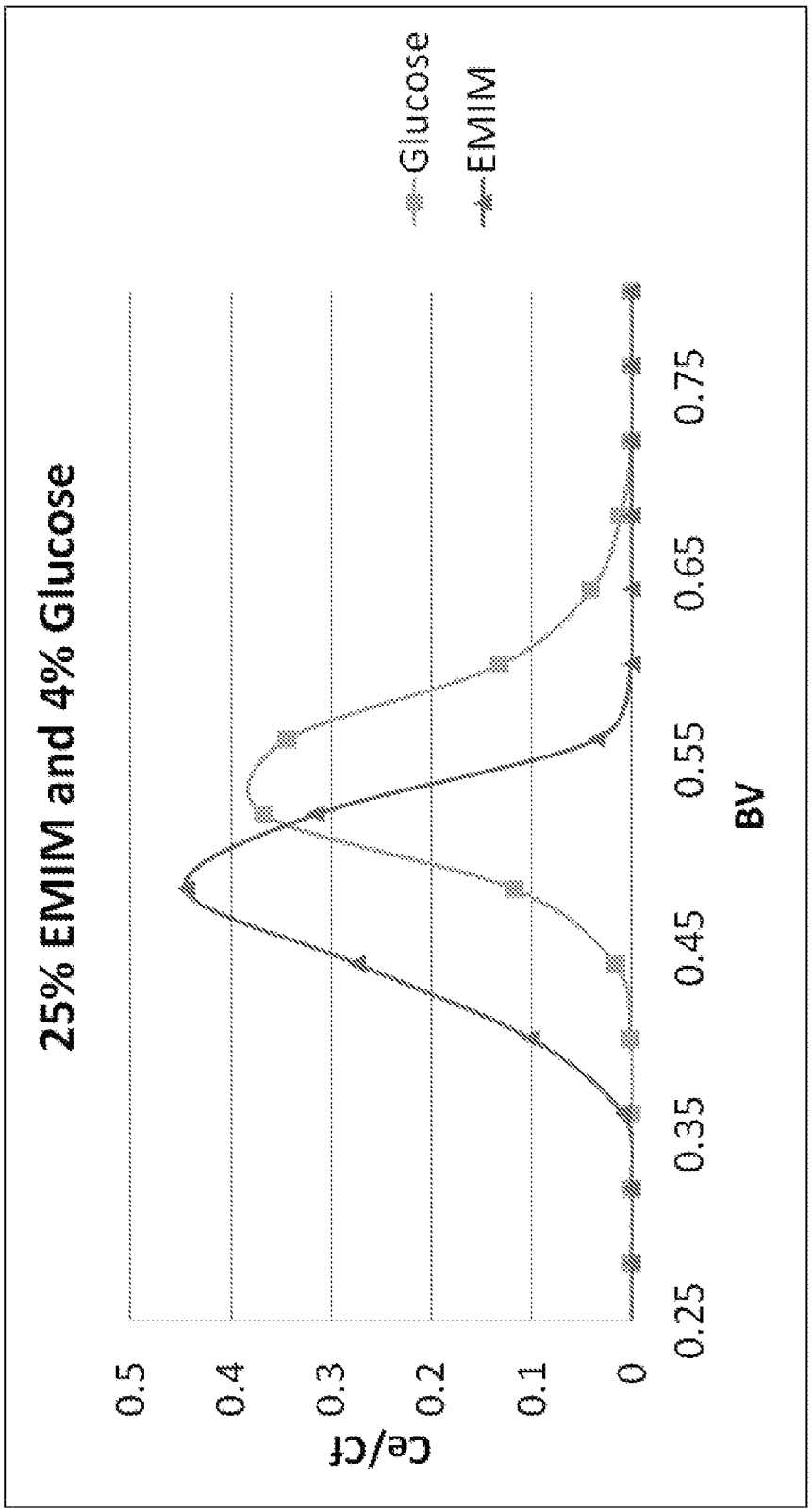
FIG. 11 illustrates results of a pulse test showing separation by chromatography of glucose and 1-ethyl-3-methylimidazolium chloride.
Figure 12:
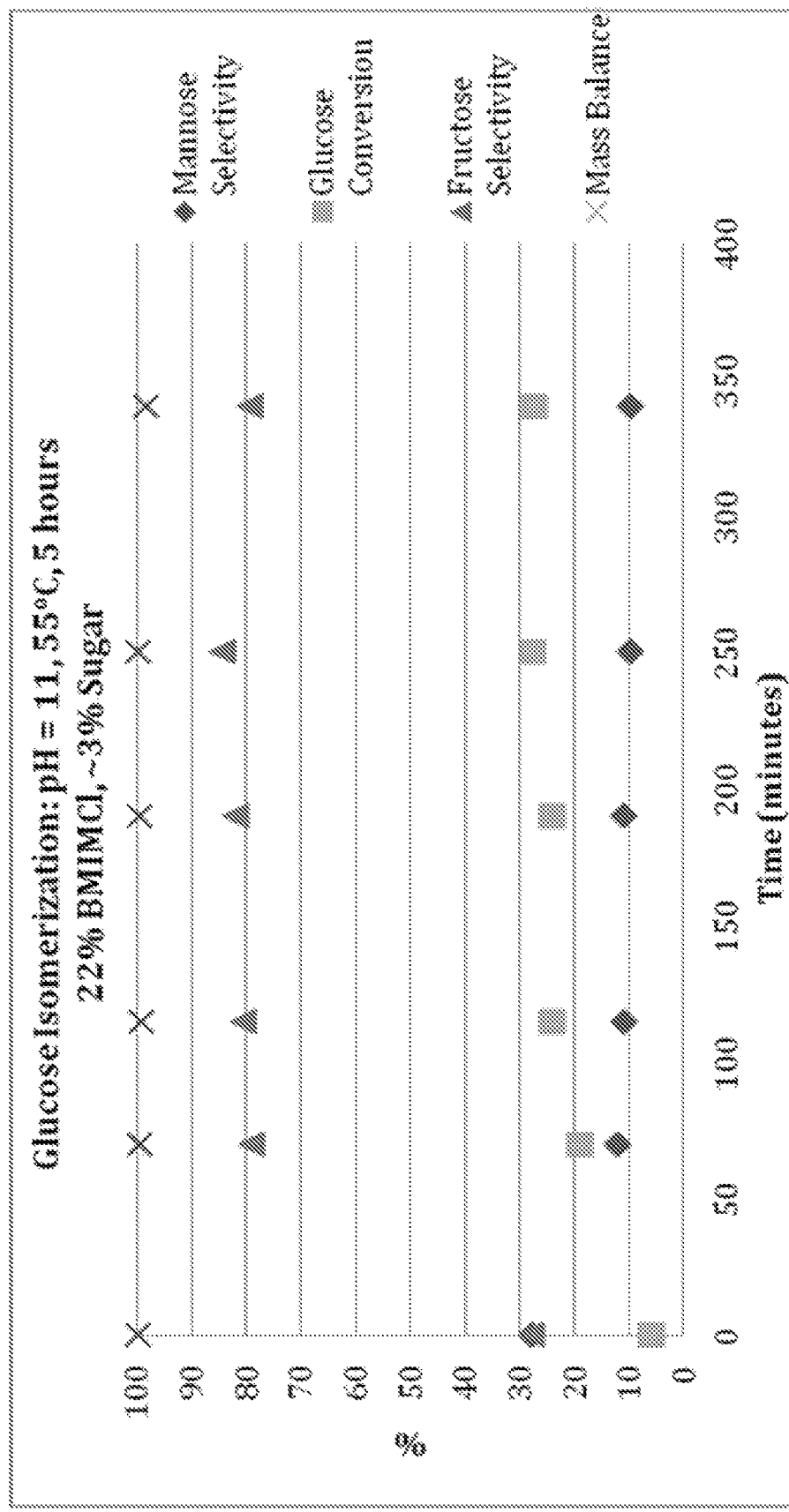
FIG. 12 illustrates a time profile of isomerization reaction of glucose to fructose in a solution comprising 1-butyl-3-methylimidazolium chloride and 1-butyl-3-methylimidazolium hydroxide.

Example 12: Chromatography Separation of Glucose and 1-Ethyl-3-Methylimidazolium Chloride A mixture of glucose and 1-ethyl-3-methylimidazolium chloride was passed through the resin PCR-642H in the 1-ethyl-3-methylimidazolium form. A 240 mL volume at diameter of 2.5 cm was used, the run conducted at 60° C. The column was eluted with deionized water at a rate of 8 ml/min. Fractions of 10 mL were collected for a total of 600 mL and analyzed by HPLC on Aminex HPX-87H column. The resulting profiles are seen in FIG. 11.

Example 13: Recovery and Refining of Glucose

A mixture of from 1 to 8% glucose, 15 to 40% 1-ethyl-3-methylimidazolium, about 1% levulinic acid, and about 1% formic acid is fed into a strong acid cation resin chromatography unit. A solution with a reduced 1-ethyl-3-methylimidazolium concentration of 0.5 to 5% is produced, and subsequently contacted with a second strong acid cation resin chromatography unit to capture residual 1-ethyl-3-methylimidazolium cations. The pH of the resulting mixture is neutralized to from 6 to 7 and residual levulinic and formic acids are removed using an amine extraction organic phase. Activated carbon is used to remove remaining organic impurities. The mixture is evaporated in an evaporation unit to yield 40% dissolved solids, and a solution of 90% glucose in water.

Example 14: Recycling of Ionic Liquid for Cellulose Solubilizing 2-ethyl-1-hexanol is added to a stream of 1-butyl-3-methylimidazolium, water, and sugars. The stream is fed to a distillation unit where Azeotropic distillation is performed to remove 1-butyl-3-methylimidazolium, using a vacuum pump to adjust pressure to 125 Torr. The boiling point of 2-ethyl-1-hexanol is 185° C., and the azeotropic boiling point of both water and 2-ethyl-1-hexanol is 99.1° C. The composition of 2-ethyl-1-hexanol in the azeotrope is 20% (weight/weight), where water is the remaining 80%. 1-butyl-3-methylimidazolium is recycled to cellulose remainder pulp pretreatment. The composition of recycled 1-butyl-3-methylimidazolium is provided in Table 14.

TABLE 1

Recycled 1-butyl-3-methylimidazolium composition

|  | % (weight/weight) |
| --- | --- |
| BMIM | 96.5 |
| Cellobiose | 0.9 |
| Fructose | 0.05 |
| Hydroxymethyl furfural | 0.05 |
| Water | 1.5 |
| 2-ethyl-1-hexanol | 1 |

What is claimed is:

1. A process for conversion of cellulose pulp to hydroxymethyl furfural, the process comprising:
   separating a lignin-depleted hydrolysate stream comprising glucose, hydroxymethyl furfural, an organic acid, and water to thereby produce:
   a first stream comprising the hydroxymethyl furfural, the organic acid, and water; and
   a second stream comprising the glucose and water;
   isomerizing the glucose in the second stream to thereby produce a fructose stream;
   dehydrating fructose in the fructose stream to thereby produce a reaction product comprising hydroxymethyl furfural: and
   recycling the reaction product, the recycling comprising introducing the reaction product from the dehydrating step to the separating step.

2. The process of claim 1, wherein the separating further produces a third stream comprising water and cellobiose.

3. The process of claim 1, wherein the lignin-depleted hydrolysate stream further comprises sodium ions, wherein the sodium ions are present in an amount not greater than 5% weight/weight.

4. The process of claim 1, wherein the concentration of the glucose in the lignin-depleted hydrolysate stream is ≥6% weight/weight.

5. The process of claim 1, wherein the concentration of the hydroxymethyl furfural in the lignin-depleted hydrolysate stream is ≤3% weight/weight.

6. The process of claim 1, wherein the separating comprises simulated moving bed chromatography or sequential simulated moving bed chromatography.

7. The process of claim 6, wherein the separating comprises a strong acid cation exchange resin.

8. The process of claim 1, wherein the isomerizing comprising increasing the pH to at least 8.

9. The process of claim 8, wherein the increasing the pH comprises adding an ionic liquid in hydroxide form.

10. The process of claim 1, wherein the isomerizing comprises 0.5 to 10 hours of stirring at a temperature between 45 to 80° C.

11. The process of claim 1, wherein the dehydrating comprises a strong acid cation resin.

12. The process of claim 11, wherein the strong acid cation resin is a macroporous strong acid cation resin.

13. The process of claim 1, wherein the fructose stream comprises fructose and glucose.

14. The process of claim 13, wherein the dehydrating comprises converting at least 50% of the fructose to hydroxymethyl furfural, wherein at least 60% of the glucose is not converted to hydroxymethyl furfural.

15. The process of claim 13, wherein the fructose stream comprises 4-10% glucose weight/weight and 1-4% fructose weight/weight.

16. The process of claim 1, wherein the reaction product comprises 3-10% glucose weight/weight, ≤0.2% fructose weight/weight, and 1-3% hydroxymethyl furfural weight/weight.

17. The process of claim 1, further comprising capturing the hydroxymethyl furfural from the first stream, the capturing comprising adsorbing on a non-functional polymeric resin the hydroxymethyl furfural from the first stream.

18. The process of claim 17, further comprising recovering the captured hydroxymethyl furfural, the recovering comprising solvent desorption.

19. The process of claim 17, wherein the capturing further comprises controlling the pH of the reaction product to be above the pKa of the organic acid.

20. The process of claim 17, further comprising increasing the pH of the first stream prior to the capturing.

21. The process of claim 20, wherein the increasing the pH comprises adding an ionic liquid in hydroxide form.

22. The process of claim 18, wherein the solvent desorption comprises addition of a solution of a solvent and water to the non-functional polymeric resin.

23. The process of claim 22, wherein the solvent is selected from ethyl acetate, methanol, ethanol, isopropanol, 1-butanol, 2-butanol, and combinations thereof.

24. The process of claim 1, wherein the first stream comprises ≤5% weight/weight hydroxymethyl furfural.

* * * * *